(12) United States Patent
Cao

(10) Patent No.: US 12,329,807 B2
(45) Date of Patent: Jun. 17, 2025

(54) DEAD ANTIGEN STIMULATED IMMATURE HETEROGENOUS DENDRITIC CELLS AS THERAPEUTICS FOR DISEASES

(71) Applicant: MegaNano Biotech, Inc., Tampa, FL (US)

(72) Inventor: Chuanhai Cao, Tampa, FL (US)

(73) Assignee: MegaNano Biotech, Inc., Tampa, FL (US)

(*) Notice: Subject to any disclaimer, the term of this patent is extended or adjusted under 35 U.S.C. 154(b) by 800 days.

(21) Appl. No.: 16/959,013

(22) PCT Filed: Jan. 18, 2019

(86) PCT No.: PCT/US2019/014352
§ 371 (c)(1),
(2) Date: Jun. 29, 2020

(87) PCT Pub. No.: WO2019/144047
PCT Pub. Date: Jul. 25, 2019

(65) Prior Publication Data
US 2020/0338173 A1    Oct. 29, 2020

Related U.S. Application Data

(60) Provisional application No. 62/619,018, filed on Jan. 18, 2018.

(51) Int. Cl.
| | | |
|---|---|---|
| A61K 39/00 | (2006.01) | |
| A61K 35/15 | (2025.01) | |
| A61K 40/19 | (2025.01) | |
| A61K 40/22 | (2025.01) | |
| A61K 40/24 | (2025.01) | |
| A61K 40/41 | (2025.01) | |
| A61K 40/42 | (2025.01) | |
| A61P 25/28 | (2006.01) | |
| C12N 5/0784 | (2010.01) | |

(52) U.S. Cl.
CPC .......... *A61K 39/0007* (2013.01); *A61K 40/19* (2025.01); *A61K 40/22* (2025.01); *A61K 40/24* (2025.01); *A61K 40/416* (2025.01); *A61K 40/42* (2025.01); *A61P 25/28* (2018.01); *C12N 5/064* (2013.01); *A61K 35/15* (2013.01); *A61K 2039/545* (2013.01); *A61K 2039/572* (2013.01); *A61K 2039/575* (2013.01)

(58) Field of Classification Search
CPC .......... A61K 39/0005; A61K 39/0007; A61K 39/0011; A61K 2039/545; A61K 2039/572; A61K 2039/575; A61K 2039/5154; A61K 39/461; A61K 39/4615; A61K 39/4622; A61K 35/15; A61P 25/28
See application file for complete search history.

(56) References Cited

U.S. PATENT DOCUMENTS

| | | |
|---|---|---|
| 4,554,101 A | 11/1985 | Hopp |
| 5,580,859 A | 12/1996 | Felgner et al. |
| 5,679,647 A | 10/1997 | Carson et al. |
| 5,703,055 A | 12/1997 | Felgner et al. |
| 5,851,756 A | 12/1998 | Steinman et al. |
| 5,994,126 A | 11/1999 | Steinman et al. |
| 8,188,046 B2 * | 5/2012 | Cao .................. C07K 14/4711 514/21.3 |
| 2005/0042996 A1 | 11/2005 | Serody et al. |
| 2006/0057129 A1 | 3/2006 | Lebkowski et al. |
| 2007/0134219 A1 | 6/2007 | Karlsson-Parra et al. |
| 2008/0014176 A1 | 1/2008 | Di Mauro et al. |
| 2008/0160050 A1 | 7/2008 | Hasumi |
| 2013/0216584 A1 | 8/2013 | Kirkin et al. |
| 2015/0335679 A1 | 11/2015 | Maurizo |
| 2016/0263206 A1 | 9/2016 | Decker et al. |

FOREIGN PATENT DOCUMENTS

| | | | |
|---|---|---|---|
| CN | 1446583 | 10/2003 | |
| CN | 102439137 | 5/2012 | |
| CN | 105452449 | 3/2016 | |
| CN | 106309369 | 1/2017 | |
| CN | 106687583 | 5/2017 | |
| EP | 1111039 | 6/2001 | |
| WO | WO 97/29182 | 8/1997 | |
| WO | WO-2008005859 A2 * | 1/2008 | ............. A61K 35/12 |
| WO | WO-2013107854 A1 * | 7/2013 | ............. A61K 39/12 |
| WO | WO 2014/096033 | 6/2014 | |

OTHER PUBLICATIONS

Xia Y et al. Rheumatology, 50:2187-2196. (Year: 2011).*
Dudek AM et al. Immature, semi-mature, and fully mature dendritic cells: toward a DC-cancer cells interface that augments anticancer immunity. Front Immunol. 2013, vol. 4, Article 438, pp. 1-14. (Year: 2013).*
Lutz MB et al. Immature, semi-mature and fully mature dendritic cells: which signals induce tolerance or immunity? Trends Immunol. 2002, 23(9)L445-449. (Year: 2002).*
Broeke et al., "MHC Class II Antigen Presentation by Dendritic Cells Regulates through Endosomal Sorting," Cold Spring Harb Perspect Biol., 2013, 5:12:: a016873 p. 1-21.
Cao et al., "Mutant Amyloid-beta-sensitized dendritic cells as Alzheimer's disease vaccine," Journal of neuroimmunology. Aug. 30, 2008,200:1:2:1-0.
Donnelly et al., DNA vaccines. Annual review of immunology. Apr. 1997;15(1):617-48.
Heagerty et al., "Time-dependent ROC curves for censored survival data and a diagnostic marker," Biometrics, Jun. 2000, 56:2:337-44.
Kyte et al., "A simple method for displaying the hydropathic character of a protein," Journal of molecular biology, May 5, 1982, 157:1:105-32.

(Continued)

*Primary Examiner* — Kimberly Ballard
(74) *Attorney, Agent, or Firm* — James Rogers

(57) ABSTRACT

Disclosed herein are exogenous antigen sensitized immature dendritic cells. The dendritic cell may also be dead. The exogenous antigen sensitized immature dendritic cells may be used to elicit an increased immune response. Further provided are vaccines comprising the exogenous antigen sensitized immature dendritic cells, methods, of inducing an immune response in a patient, and methods of treating a disease.

16 Claims, 18 Drawing Sheets

(56) References Cited

OTHER PUBLICATIONS

Pandha, et al., "Dendritic cell immunotherapy for urological cancers using cryopreserved allogeneic tumour lysate-pulsed cells: a phase I/II study," BJU Int., Aug. 2004, 94:412-418.
PCT International Search Report and Written Opinion in International Appln. No. PCT/US2019/014352, dated Jun. 10, 2019, 14 pages.
PCT International Search Report on Patentability in International Appln. No. PCT/US2019/014352, dated Jul. 21, 2020, 12 pages.
Remington's Pharmaceutical Sciences, 15th Ed. 1975, pp. 335-337.
Wenninger et al., "C.T.F.A. Cosmetic Ingredient Handbook," 1992, pp. 587-592.
Wilson et al., "Dendritic cells constitutively present self antigens in their immature state in vivo and regulate antigen presentation be controlling the rates of MHc class II synthesis and endocytosis," Blood, 2004, 103(6): p. 2187-95.
Zacca et al. "Aging impairs the Ability of Conventional Dendritic Cells to Cross-Prime CD8+ T Cells upon Stimulation with a TLR7 Ligand, " PLosOne, 2015, 10:10::e0140672, pp. 1-20.
Brezovakova et al., "Dendritic cells as an alternate approach for treatment of neurodegenerative disorders," Cellular and molecular neurobiology, Aug. 2018, 38(6): 8 pages.
Extended European Search Report in European Appln. No. 197409634, Sep. 16, 2021, 10 pages.
Hirschowitz et al., "Immunization of NSCLC patients with antigen-pulsed immature autologous dendritic cells," Lung cancer, Sep. 1, 2007, 57(3):365-372.
Luo et al., "Efficacy of a therapeutic vaccine using mutated β-amyloid sensitized dendritic cells in Alzheimer's mice," Journal of Neuroimmune Pharmacology, Sep. 2012, 7(3):640-655.
Wang et al., "The combined treatment of amyloid-β1-42-stimulated bone marrow-derived dendritic cells plus splenocytes from young mice prevents the development of Alzheimer's disease in APPswe/PSENIdE9 mice," Neurobiology of aging, Jan. 1, 2015, 36(1):111-122.

* cited by examiner

DEAD ANTIGEN STIMULATED IMMATURE HETEROGENOUS DENDRITIC CELLS AS THERAPEUTICS FOR DISEASES

CROSS-REFERENCE TO RELATED APPLICATIONS

This application is a National Stage application under 35 U.S.C. § 371 of International Application No. PCT/US2019/014352, filed Jan. 18, 2019, which claims priority to U.S. Provisional Patent Application No. 62/619,018, filed Jan. 18, 2018, which is incorporated herein by reference in their entirety.

FIELD

This disclosure relates to dendritic cells, vaccines, and therapeutics comprising the same.

INTRODUCTION

Antigen sensitized dendritic cells (DCs) have been studied and used as vaccines to treat various diseases. However, some reports indicated that induction of immunity required mature dendritic cells, whereas immature dendritic cells have been reported to induce immunity poorly or result in poor clinical outcomes in the context of cancer or viral infections. Conventional vaccines have also included live DCs. However, the understanding of DC function in immune modulation and response has been limited and few therapies have successfully progressed to clinical application.

SUMMARY

In an aspect, the disclosure relates to a vaccine for a patient. The vaccine may include an antigen sensitized immature dendritic cell, wherein the dendritic cell is exogenous to the patient. In some embodiments, the dendritic cell is from a subject of the same species as the patient. In some embodiments, the dendritic cell is from a subject that is younger than the patient and of the same species as the patient. In some embodiments, the dendritic cell is from a subject of a different species than the patient. In some embodiments, the dendritic cell is dead. In some embodiments, the dendritic cell was killed by sonication, heat treatment, lyophilization, or a combination thereof. In some embodiments, the dendritic cell is a lysed cell or a portion thereof. In some embodiments, the dendritic cell has not been matured by stimulation with cytokines selected from TNFα, IL6, and IL1α. In some embodiments, the vaccine induces an increased immune response compared to a vaccine comprising a mature dendritic cell. In some embodiments, the vaccine induces an immune response similar to a response induced by a vaccine comprising a dendritic cell that is autologous to the patient. In some embodiments, the dendritic cell is antigen sensitized by contacting with the antigen. In some embodiments, the dendritic cell is contacted with the antigen in vitro. In some embodiments, the antigen comprises a peptide, a protein, a carbohydrate, a lipid, or a combination thereof. In some embodiments, the antigen comprises a peptide. In some embodiments, the dendritic cell is derived from blood or bone marrow. In some embodiments, the dendritic cell is a monocyte-derived immature dendritic cell.

In a further aspect, the disclosure relates to a method of inducing an immune response in a patient. The method may include administering to the patient a vaccine as detailed herein. In some embodiments, the vaccine activates a T cell response, T cell immunity, a B cell response, or a combination thereof. In some embodiments, the vaccine is administered to the patient in multiple doses. In some embodiments, the vaccine is administered to the patient bi-weekly. In some embodiments, the patient has a disease selected from cancer, autoimmune disease, infectious disease, and neurological disease. In some embodiments, the neurological disease comprises Alzheimer's Disease (AD).

Another aspect of the disclosure provides a method of formulating a vaccine. The method may include obtaining an immature dendritic cell; contacting the immature dendritic cell with an antigen to form an immature antigen sensitized dendritic cell; and formulating the vaccine comprising the immature antigen sensitized dendritic cell and a pharmaceutically acceptable carrier. In some embodiments, the method further includes killing the immature antigen sensitized dendritic cell. In some embodiments, killing comprises sonication, heat treatment, lyophilization, or a combination thereof. In some embodiments, the dendritic cell is derived from blood or bone marrow. In some embodiments, the dendritic cell is a monocyte-derived immature dendritic cell.

The disclosure provides for other aspects and embodiments that will be apparent in light of the following detailed description and accompanying figures.

BRIEF DESCRIPTION OF THE DRAWINGS

FIG. 1A is the flow cytometer result of dendritic cell maturation. Cell surface markers used for this were CD80, CD86, MHCII, and CD11 b. Cytokines used for maturation were human IL1α, IL6, and TNFα. FIG. 1B is the ELISA result for Anti-Aβ antibody detection post vaccination with peptide (Aβ) sensitized immature dendritic cells (labeled as "PBMC+Hu 22W"), peptide sensitized matured dendritic cells (labeled as "PBMC+Hu 22W+cyto"), matured dendritic cells (labeled as "PBMC+cyto") and immature dendritic cells (labeled as "PBMC Ctr"). Only the peptide sensitized immature dendritic cells as a vaccine induced an antibody response, and the mature dendritic cells failed to induce antibody response.

FIG. 2A is the antibody response against human Aβ42 with a mutation at the 22 amino acid (22W) after 2 vaccinations with either the whole peptide sensitized dendritic cells or the same batch of cells lysed by sonication for 10 seconds. The dendritic cells were prepared from 2 month old BALB/c mice bone marrow by following Cao et al. (Cao C., et al. *J. Neuroimmunol.* 2008, 200, 1-10). Then $1 \times 10^6$ whole cells or lysed cells were injected into 2 month old BALB/c mice, then boosted two weeks later with the same vaccine. Blood were collected 10 days after the second vaccination. Two mice (n=2) were injected with whole cells by intraperitoneal injection, and three mice were injected with cell debris (the antigen sensitized: n=3). Both the whole cell and lysed cell debris induced high antibody response and, as seen in the left panel graph, there was no significant difference between the two groups (P>0.05). FIG. 2B is the epitope mapping against all mutant peptide and the fragments. We selected one plasma from each group and tested the antibody against different peptides. As it is shown in the graph, there was no difference between two sera against all peptides, so the epitope was the same. The right graph in FIG. 2B shows results from the epitope mapping against wild-type Aβ peptide fragments tested to the same two anti-sera shown in the left graph of FIG. 2B. Again, there was no difference between the two anti-sera. FIG. 2C is the flow cytometer result of whole cell versus sonicated cells. The particle size was much smaller than the whole cell, so the majority cells were disrupted by sonication.

FIG. 5A is a graph showing the antibody response after DC vaccination in old and young mice. Immature Aβ 22W sensitized DC cell debris was injected into 3 month old C57/BL6 mice and 18 month old C57/BL6 mice bi-weekly. Blood was taken 10 days after the second injection, and antibody response was detected against wild-type amyloid beta 1-42 peptide. The results indicated that the young mice had more antibody response than the old mice (P<0.05, n=4). FIG. 5B, FIG. 5C, and FIG. 5D are graphs of flow cytometry results. Dendritic cells were prepared from GFP transgenic mice and injected into C57/BL6. Blood was drawn and tested by flow cytometry to track cells with florescent GFP. There were no positive GFP cells in the blood.

DETAILED DESCRIPTION

Figure 1A:
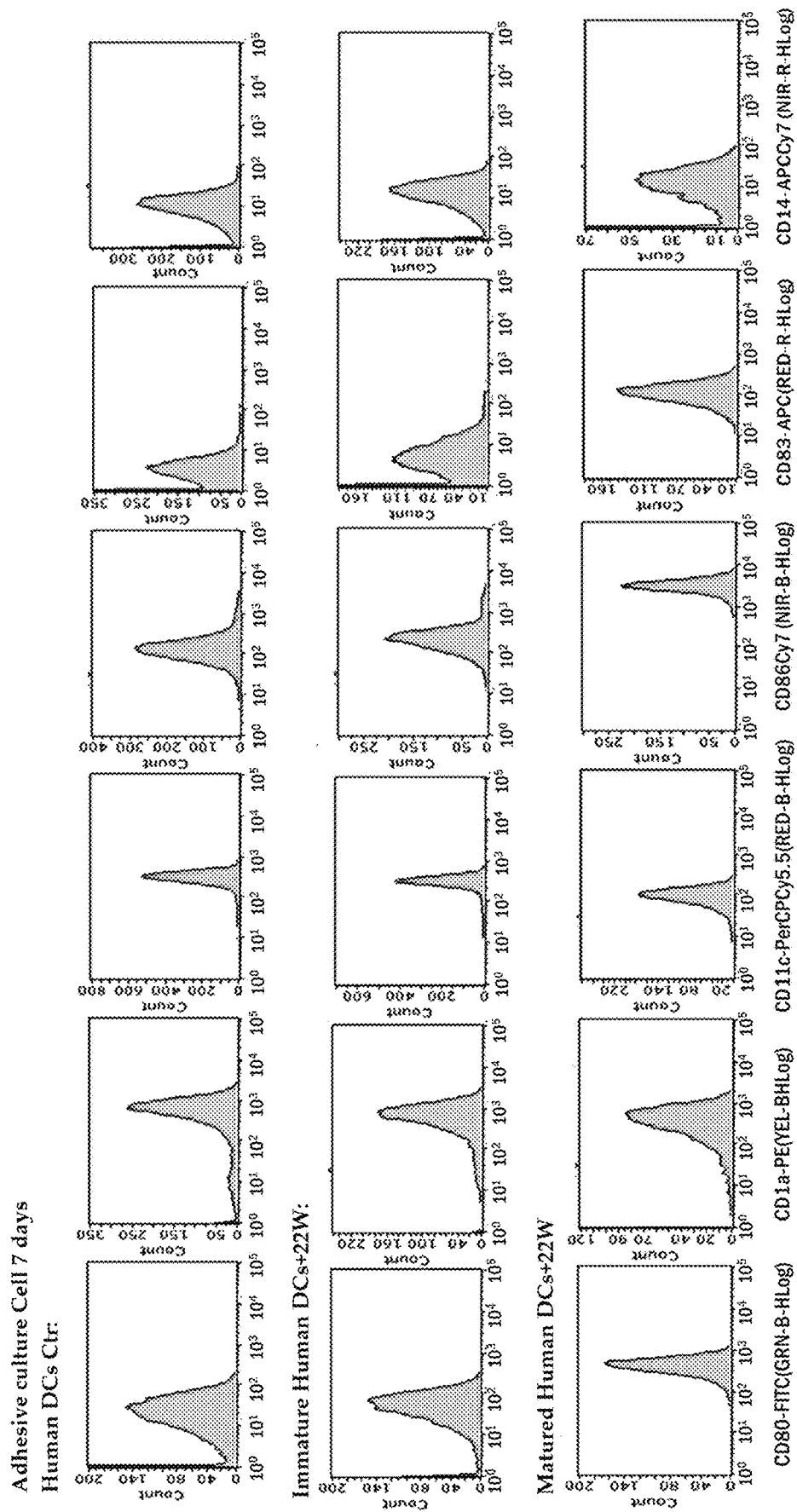
FIG. 1A and FIG. 1B are two graphs showing the flow result of dendritic cell maturation and immune response of peptide sensitized mature and immature dendritic cells as vaccines.

Described herein are vaccines comprising exogenous antigen sensitized immature dendritic cells, which induce an improved antibody response compared to conventional vaccines and may be used as therapeutics for various diseases. The vaccine may include antigen sensitized dendritic cells from a species different from the patient to which the vaccine is administered. It was found that antigen sensitized immature dendritic cells elicit an earlier and better immunoresponse than mature dendritic cells. It was also discovered that lysed antigen sensitized dendritic cells work as well as live antigen sensitized dendritic cells in inducing an immunoresponse, and that exogenous dendritic cells have no adverse effects on the recipient, a patient, when used as a therapy relative to autologous dendritic cells. A universal lyophilized dendritic cell lysate may be used as a vaccine, instead of being limited to vaccines with live autologous dendritic cells. Dead exogenous antigen sensitized immature dendritic cells, or a portion thereof, as detailed herein may be used for vaccines and therapies, and they may significantly reduce the cost of storage, transport, preparation, and transfer, and increase the availability, universality, and effectiveness compared to conventional vaccines.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4. In some embodiments, the term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "amyloid-beta", "amyloid beta", "A-beta", "Abeta", or "Aβ" as used interchangeably herein refers to a peptide of from 36 to 43 amino acids that is found in the brain. Amyloid-beta is formed after sequential cleavage of the amyloid precursor protein (APP), a transmembrane glycoprotein, by the β- and γ-secretases. The most common isoforms of the amyloid-beta peptide are 40 amino acids in length (Aβ40) and 42 amino acids in length (Aβ42). The Aβ40 form is the more common of the two forms, but Aβ42 may be more fibrillogenic. Aggregation of amyloid-beta may lead to Alzheimer's disease.

"Autoimmune disease" or "autoimmune disorder" refers to a condition arising from an abnormal immune response to a normal body part. Autoimmune diseases may include, for example, rheumatoid arthritis (RA), systemic lupus erythematosus, inflammatory bowel disease, Type 1 diabetes mellitus, Guillain-Barre syndrome, chronic inflammatory demyelinating polyneuropathy, psoriasis, Grave's disease, Hashimoto's thyroiditis, myasthenia gravis, vasculitis, and multiple sclerosis (MS).

As used herein, "cancer" may include any cell or tissue derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state. Examples of solid tumors may include fibrosarcoma, myxosarcoma, iiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcmoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. Additional cancers may include blood borne cancers such as acute lymphoblastic leukemia (ALL), acute lymphoblastic B-cell leukemia, acute lymphoblastic T-cell leukemia, acute myeloblastic leukemia (AML), acute promyelocyte leukemia (APL), acute monobiastic leukemia, acute erythroleukemic leukemia, acute megakaryoblastic leukemia, acute myelomonocytic leukemia, acute nonlyrnphocyctic leukemia, acute undifferentiated leukemia, chronic myelocytic leukemia (CML), chronic lymphocytic leukemia (CLL), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target or for an activity may be defined in accordance with standard practice. A control may be a mature dendritic cell or subject who has been administered a mature dendritic cell. A control may be a live dendritic cell or subject who has been administered a live dendritic cell. A control may be a non-antigen stimulated dendritic cell or subject who has been administered a non-antigen stimulated dendritic cell. A control may be a subject without a dendritic cell as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

"Immune response" response refers to the activation of a subject's immune system, e.g., that of a mammal, in response to the introduction of antigen. The immune response can be in the form of a cellular or humoral response, or both.

"Infectious disease" refers to an illness resulting from an infection. An infection is the invasion of a subject's tissues by disease-causing agents, their multiplication, and the reaction of the subject's tissues to the infectious agents and the toxins they produce. Infectious agents may include viruses, viroids, prions, bacteria, protozoans, nematodes such as parasitic roundworms and pinworms, arthropods such as ticks, mites, fleas, and lice, fungi such as ringworm, and other macroparasites such as tapeworms and other helminths. Infectious diseases may include, but are not limited to, infectious diseases caused by any type of microorganism such as bacteria, fungi (for example, candidiatis, aspergilosis) and viruses (for example, herpes viruses-related disorders, HIV-related diseases, influenza), by parasites (for example, malaria, amebiasis) or by prions (for example, Creutzfeld-Jacob Disease).

"Neurological disorder" refers to a central nervous system (CNS) disorder characterized or caused by damaged, defective, malfunctioning, or deficient neural cells. As used herein, a disease or disorder of the CNS refers to a disorder affecting either the spinal cord (e.g., a myelopathy) or brain (e.g., an encephalopathy) of a subject, which may present with neurological and/or psychiatric symptoms. CNS disorders include many various neurodegenerative diseases and psychiatric disorders. In some embodiments, the disease or disorder is a developmental disorder, a cognitive disorder, a degenerative disorder, a neuropsychiatric disorder, or brain injury. In some embodiments, the developmental disorder is Lissecephaly. In some embodiments, the cognitive disorder is selected from Angelman Syndrome and schizophrenia. In some embodiments, the degenerative disorder is Alzheimer's disease. In some embodiments, the neuropsychiatric disorder is selected from schizophrenia and bipolar disorder. In some embodiments, the brain injury is traumatic brain injury (TBI). In some embodiments, the disease or disorder is selected from Lissecephaly, fragile X syndrome, William's syndrome, Rett syndrome, Down's syndrome, Angelman syndrome, autism, ischemia, epilepsy, hypoxia, Parkinson's Disease, Huntington's Disease, Alzheimer's Disease, Reelin deficiency, schizophrenia, bipolar disorder, neurodegeneration, head and spinal cord injury, traumatic brain injury, mental retardation, dementia, bipolar disorder, stroke, multiple sclerosis, amyotrophic lateral sclerosis, neurogenic disorders, drug-induced neurotoxicity, toxin-induced neurotoxicity, eye injury, retinopathy, and age-related cognitive decline.

A "pharmaceutically acceptable excipient," "pharmaceutically acceptable diluent," "pharmaceutically acceptable carrier," or "pharmaceutically acceptable adjuvant" as used interchangeably herein means an excipient, diluent, carrier, and/or adjuvant that is useful in preparing a pharmaceutical composition that is generally safe, non-toxic, and neither biologically nor otherwise undesirable, and includes an excipient, diluent, carrier, and adjuvant that is acceptable for veterinary use and/or human pharmaceutical use, such as those promulgated by the United States Food and Drug Administration.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Sample" or "test sample" as used herein can mean any sample in which the presence and/or level of a target is to be detected or determined or any sample comprising DC as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described DCs or methods. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. In some embodiments, the subject is human. The subject may be of any age or stage of development, such as, for example, an adult, an adolescent, or an infant. In some embodiments, the subject has a specific genetic marker. The subject may be diagnosed with or at risk of developing disease. The subject or patient may be undergoing other forms of treatment.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Treat," "treatment," or "treating," when referring to protection of a subject from a disease, means suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. Dendritic Cells

Dendritic cells (DCs) are antigen-presenting cells (APCs). The main function of DCs is to process antigen material and present it on the cell surface to the T cells of the immune system. DCs act as messengers between the innate and the adaptive immune systems and are important for eliciting T cell mediated immune responses. DCs may also be referred to as professional APCs. DCs may be present in the tissues that are in contact with the external environment, such as the skin, the inner lining of the nose, lungs, stomach, and intestines. DCs may reside in nonlymphoid tissue in an immature form where they are capable of internalizing antigens. DCs can also be found in an immature state in the blood.

In some embodiments, the DCs as detailed herein may be used as an immunomodulatory agent. In some embodiments, the DCs may be formulated into a vaccine. The DCs may be used as a therapy for various diseases. The DC may induce an increased immune response compared to a mature DC, and induce an immune response similar to that of an autologous DC.

The DCs as detailed herein may be immature, antigen sensitized, dead, or exogenous, or a combination thereof.

a. Immature Dendritic Cells

In some embodiments, the DCs as detailed herein are immature. Immature DCs have low T-cell activation potential. Immature DCs have not been stimulated with inflammatory cytokines such as, for example, TNFα, IL6, or IL1α, or a combination thereof. Stimulation with inflammatory cytokines can switch DCs to an immunostimulatory mode. This process is termed "maturation" and is associated with changes in dendritic cell phenotype and function, including up regulation of co-stimulatory and adhesion molecules and expression of distinct chemokine receptors.

In contrast, mature DCs are those that have been stimulated with inflammatory cytokines such as, for example, TNFα, IL6, or IL1α, or a combination thereof. The amount and type of cytokine used, the duration of exposure, as well as the day on which the immature dendritic cells are contacted with cytokine, can vary. Those skilled in the art may employ conventional clinical and laboratory means to optimize the effectiveness of the immature dendritic cell system. For example, the immature DC may be cultured for about 2, 3, 4, 5, 6, 7, 8, 9, or 10 days before contacting with an inflammatory cytokine. In some embodiments, the DC is cultured for about 4, 5, 6, or 7 days before contacting with an inflammatory cytokine. The DC may be then contacted with an inflammatory cytokine for about 1, 2, 3, 4, or 5 days. In some embodiments, the DC is contacted with the inflammatory cytokine for about 3 days. Antigen may be added to the tissue culture medium containing GM-CSF and/or IL4, for example. The DC may then be cultured for additional days without inflammatory cytokine exposure. Immature DCs may express little to no levels of a marker such as CD80, CD83, CD86, or a combination thereof, or at reduced levels relative to a mature DC. Immature DCs may express a marker such as CD11c at levels greater than a mature DC. Mature DCs may express a marker such as CD80, CD83, CD86, or a combination thereof, at an increased or greater level, compared to an immature DC. Mature DCs may express little to no levels of a marker such as CD11c, or at reduced levels relative to an immature DC. The immature DCs as detailed herein may induce an increased immune response compared to a mature dendritic cell. The immature DC may induce an immune response that is at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold greater than that induced by a mature DC. In some embodiments, the immature DC induces an immune response that is at least about 4-fold greater than that induced by a mature DC. In some embodiments, the immature DC induces an immune response that is at least about 5-fold greater than that induced by a mature DC. In some embodiments, the immature DC induces an immune response that is at least about 5.5-fold greater than that induced by a mature DC. In some embodiments, the immature DC induces an immune response that is at least about 6-fold greater than that induced by a mature DC. In some embodiments, the immature DC induces an immune response that is at least about 6.5-fold greater than that induced by a mature DC.

b. Antigen Sensitized Dendritic Cells

Immature DCs may be contacted with an antigen or antigens for which an increased immune response is desired, to form an antigen sensitized immature DC. The antigen may comprise a peptide, a protein, a carbohydrate, a lipid, or a combination thereof. In some embodiments, the antigen comprises a peptide.

Cultures of immature DCs may be contacted with the antigen of interest on or about day 1, 2, 3, 4, 5, 6, 7, 8, 9, or 10 of culture for a time sufficient to allow the antigen to be taken up by the immature DCs. The duration of antigen exposure can vary. The duration of antigen exposure may be, for example, less than 1-2 days with 0.1-10 μg/mL of the antigen of interest. The immature DC may then be cultured for additional days without antigen exposure. The amount of antigen used, the duration of exposure, as well as the day on which the immature dendritic cells are contacted with antigen, can vary depending on the specific antigen of interest. Those skilled in the art may employ conventional clinical and laboratory means to optimize the effectiveness of the immature dendritic cell system. As an example, immature DCs may be cultured in the presence of GM-CSF and IL4 at 37° C. and 5% $CO_2$. In some embodiments, the DC is contacted with an antigen in vitro.

After antigen uptake, DCs may be operable to migrate from non-lymphoid tissues to regional lymph nodes as a step in the generation of T cell-mediated immune responses. In the lymph nodes, DCs can interact with T cells and/or B cells to initiate and shape the adaptive immune response. DCs may activate T cells, initiate T cell immunity, initiate B cell response, or a combination thereof. DCs may activate both CD4+ helper T cells and CD8+ cytotoxic T cells.

c. Dead Dendritic Cells

Conventional DC vaccines or therapies use live DCs, often because the homing of antigen sensitized dendritic cells to the lymphatic system was considered as the essential step for initiating the immune response. As detailed in the Examples, however, once the antigen is presented in vitro, then viability of the DCs is not essential for eliciting an immune response. The DCs as detailed herein may be live cells or whole live cells. In other embodiments, the DCs as detailed herein are dead. Dead DCs are DCs not capable of growing or multiplying. The DCs may be dead whole cells, or a portion of a dead cell. Killing a DC may be performed by any suitable means known in the art. The DC may be killed by a chemical or physical method. For example, the DC may be killed by a method comprising sonication, lysing, heat treatment, lyophilization, or a combination thereof. In some embodiments, the DC is sonicated. In some embodiments, the DC is lyophilized. In some embodiments, the DC is sonicated and then lyophilized. In some embodiments, the DC is a lysed cell or a portion thereof. Dead DCs may be stored at any suitable temperature, such as any temperature 0-100° C., cold temperatures, hot temperatures, body temperature, ambient temperature, or room temperature. In some embodiments, dead DCs are stored at ambient or room temperature. Antigen sensitized immature DCs can also be cryopreserved or otherwise treated. Dead DCs may make storage and/or transport faster, easier, or more cost effective, or a combination thereof, compared to live DCs.

d. Exogenous Dendritic Cells

Conventional DC vaccines use DCs derived from autologous cells. As detailed herein, exogenous dendritic cells have no adverse effects on a patient when used as a therapy relative to autologous dendritic cells. The DC may be exogenous. "Exogenous" may also be referred to as "heterologous." "Exogenous" may mean derived from any subject that is different from the patient. "Exogenous" may refer to derivation or sourced from a subject that is a different individual from the subject of the same species, of the same genus, of the same sex, of similar age, of a different species, of a different genus, of a different sex, or of a different age, or a combination thereof, for example. The DC may be derived from a subject that is exogenous to the patient. The DC may be cross-species. The DC may be derived from a subject of the same or different species as the patient. The DC may be from a subject that is older or younger than the patient. In some embodiments, the DC is from a subject of the same species as the patient. In some embodiments, the DC is from a subject that is younger than the patient and of the same species as the patient. In some embodiments, the DC is from a subject of a different species than the patient. In some embodiments, the DC is from a subject of the same genus as the patient. In some embodiments, the DC is from a subject of a genus species than the patient. In some embodiments, the DC induces an immune response similar to a response induced by a DC that is autologous to the patient.

e. Isolation of Dendritic Cells

Methods for isolating and culturing immature DCs are disclosed in U.S. Pat. No. 5,994,126 and WO 97/29182, which are incorporated herein by reference. Briefly, appropriate tissue sources for isolating immature dendritic cells may include spleen, afferent lymph, bone marrow, blood, and cord blood, as well as blood cells elicited after administration of cytokines such as G-CSF or FLT-3 ligand. In some embodiments, the DC is derived from blood or bone marrow. In some embodiments, the DC is a monocyte-derived immature dendritic cell. In some embodiments, a tissue source may be treated prior to culturing with substances that stimulate hematopoiesis, such as, for example, G-CSF and FLT-3 ligand, in order to increase the proportion of dendritic cell precursors relative to other cell types. Other examples may include, but are not limited to, GM-CSF, M-CSF, TGF-Beta, thrombopoietin, or a combination thereof.

Pretreatment may also be used to make the tissue source more suitable for in vitro culture. Those skilled in the art would recognize that the method of treatment will likely depend on the particular tissue source. For example, spleen or bone marrow may first be treated so as to obtain single cells followed by suitable cell separation techniques to separate leukocytes from other cell types as described in U.S. Pat. Nos. 5,851,756 and 5,994,126, which are incorporated herein by reference. Treatment of blood may involve cell separation techniques to separate leukocytes from other cell types including red blood cells (RBCs). Removal of certain cells may be accomplished by standard methods known in the art.

In some embodiments, the tissue source is blood or bone marrow. In some embodiments, the tissue source is blood. In some embodiments, the tissue source is human blood.

In some embodiments, immature dendritic cells are derived from multipotent blood monocyte precursors (see, for example, WO 97/29182, incorporated herein by reference). These multipotent cells typically express CD14, CD32, CD68, and CD115 monocyte markers with little or no expression of CD83, or p55, or accessory molecules such as CD40 and CD86. When cultured in the presence of cytokines such as a combination of GM-CSF and IL-4 or IL-13 as described below, the multipotent cells may give rise to the immature dendritic cells. The immature dendritic cells can be modified (for example using vectors expressing IL-10), to keep them in an immature state in vitro or in vivo.

Those skilled in the art would recognize that any number of modifications may be introduced to the disclosed methods for isolating immature dendritic cells and maintaining them in an immature state in vitro and in vivo having regard to the objects of the several embodiments of the invention here disclosed.

f. Culturing of Dendritic Cells

Cells obtained from the appropriate tissue source may be cultured to form a primary culture, for example, on an appropriate substrate in a culture medium supplemented with granulocyte/macrophage colony-stimulating factor (GM-CSF), a substance which can promote the differentiation of pluripotent cells to immature DCs as described in U.S. Pat. Nos. 5,851,756 and 5,994,126, which are incorporated herein by reference. In some embodiments, the substrate includes any tissue compatible surface to which cells may adhere. For example, the substrate may be a commercial plastic treated for use in tissue culture.

To further increase the yield of immature DCs, other factors, in addition to GM-CSF, may be added to the culture medium to block or inhibit proliferation of non-dendritic cell types. Example of factors that inhibit non-dendritic cell proliferation may include Interleukin-4 (IL-4) and/or Interleukin-13 (IL-13), which may inhibit macrophage proliferation. A combination of these substances may increase the number of immature DCs present in the culture by preferentially stimulating proliferation of the DC precursors, while at the same time inhibiting growth of non-dendritic cell types.

In some embodiments, an enriched population of immature DCs can be generated from blood monocyte precursors, for example, by plating mononuclear cells on plastic tissue culture plates and allowing them to adhere. The plastic adherent cells may then be cultured in the presence of GM-CSF or IL-4, or a combination thereof, in order to expand the population of immature DCs. GM-CSF at a concentration of between about 200 U/mL to about 2000 U/mL, between about 500 U/mL to about 1000 U/mL, or between about 800 U/mL and about 1000 U/mL may produce significant quantities of the immature DCs. IL-4 at a concentration of between about 200 U/mL to about 2000 U/mL, between about 500 U/mL to about 1000 U/mL, or between about 800 U/mL and about 1000 U/mL may produce significant quantities of the immature DCs. A combination of GM-CSF (10 ng/mL) and IL-4 (10-20 ng/mL) may be used. The concentration of cytokines may be varied at different stages of the culture such that freshly cultured cells are cultured in the presence of higher concentrations of IL-4 (1000 U/mL) than established cultures (500 U/mL IL-4 after 2 days in culture). Other cytokines such as IL-13 may be substituted for IL-4.

The cultured immature DCs may not label with mAb markers found on mature dendritic cells. Examples of markers for mature DCs include, expression of surface CD83, DC-LAMP, p55, CCR-7, and expression of high levels of MHCII and costimulatory molecules, such as, for example, CD86. Immature DCs may be identified based on typical morphology, expression of lower levels of MHCII and costimulatory molecules, and the lack of expression of DC maturation markers, e.g., surface expression of CD83 and expression of DC-LAMP, and lack of CD14 expression. In addition, examples of positive markers for immature DCs include, but are not limited to, DC-SIGN, intracellular CD83, Langerin, and CD1A.

Thus, by utilizing standard antibody staining techniques known in the art, it is possible to assess the proportion of immature DCs in any given culture. Antibodies may also be used to isolate or purify immature DCs from mixed cell cultures by flow cytometry or other cell sorting techniques well known in the art.

g. Increased Immune Response

Once in the lymph nodes, DCs can interact with T cells and/or B cells to initiate and shape the adaptive immune response. DCs may activate T cells, initiate T cell immunity, initiate B cell response, or a combination thereof. DCs may activate both CD4+ helper T cells and CD8+ cytotoxic T cells. The DCs may be immature, antigen sensitized, dead, exogenous, or a combination thereof, and may induce an increased immune response compared to a mature DC and/or induce an immune response similar to that of an autologous DC. The DCs as detailed herein may induce an increased or enhanced immune response compared to conventional DCs or other control. An increased or enhanced immune response may refer to an earlier response, a response that is longer in duration, or a response with increased levels of certain antibodies or cytokines. For example, the DCs as detailed herein may increase the level of antibodies specific for the antigen, relative to a control. The DCs as detailed herein may cause the presence of antibodies specific for the antigen to be detected earlier, relative to a control. As another example, the DCs as detailed herein may increase the level of cytokines, relative to a control.

In some embodiments, the immune response elicited by the DCs as detailed herein begin earlier than conventional DCs or other control. The immune response elicited by the DCs as detailed herein may begin at least about 3 days, at least about 5 days, at least about one week, at least about 1.5 weeks, at least about two weeks, or at least about 2.5 weeks earlier than conventional DCs or other control. The immune response elicited by the DCs as detailed herein may begin at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 2-fold, at least about 3-fold, at least about 4-fold, at least about 4.5-fold, at least about 5-fold, at least about 6-fold, at least about 7-fold, at least about 8-fold, at least about 9-fold, or at least about 10-fold earlier than conventional DCs or other control.

The DC as detailed herein may induce an immune response that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold enhanced or greater than that induced by conventional DCs or other control. In some embodiments, the DC as detailed herein induce an immune response that is at least about 4-fold enhanced or greater than that induced by conventional DCs or other control. In some embodiments, the DC as detailed herein induce an immune response that is at least about 5-fold enhanced or greater than that induced by conventional DCs or other control. In some embodiments, the DC as detailed herein induce an immune response that is at least about 5.5-fold enhanced or greater than that induced by conventional DCs or other control. In some embodiments, the DC as detailed herein induce an immune response that is at least about 6-fold enhanced or greater than that induced by conventional DCs or other control. In some embodiments, the DC as detailed herein induce an immune response that is at least about 6.5-fold enhanced or greater than that induced by conventional DCs or other control.

3. Pharmaceutical Compositions

The DCs as detailed herein may be formulated into pharmaceutical compositions in accordance with standard techniques well known to those skilled in the pharmaceutical art. The composition may comprise the DC and a pharmaceutically acceptable carrier. The term "pharmaceutically acceptable carrier," as used herein, means a non-toxic, inert solid, semi-solid or liquid filler, diluent, encapsulating material or formulation auxiliary of any type. The pharmaceutical composition may include DCs sensitized to one or more different antigens. In some embodiments, the pharmaceutical composition includes DCs sensitized to a first antigen, and other DCs sensitized to a second antigen.

The route by which the disclosed DCs are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). In some embodiments, the pharmaceutical composition is for administration to a subject's central nervous system. Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof. The pharmaceutical composition may include one or more adjuvants as known in the art.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may typically be about 0.1 to about 10%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, PA) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

Although the amounts of components in the compositions may vary depending on the type of composition prepared, in general, systemic compositions may include 0.01% to 50% of a compound (e.g., a compound of Formula I' or I or II or III) and 50% to 99.99% of one or more carriers. Compositions for parenteral administration may typically include 0.1% to 10% of a compound and 90% to 99.9% of one or more carriers. Oral dosage forms may include, for example, at least about 5%, or about 25% to about 50% of a compound. The oral dosage compositions may include about 50% to about 95% of carriers, or from about 50% to about 75% of carriers. The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

a. Vaccines

The immature antigen sensitized dendritic cell may be formulated into a vaccine, according to methods known in the art. The vaccine may include DCs sensitized to one or more different antigens. In some embodiments, the vaccine includes DCs sensitized to a first antigen, and other DCs sensitized to a second antigen.

4. Administration

The DCs as detailed herein, or the pharmaceutical compositions comprising the same, may be administered to a subject or patient. Such compositions comprising a DC can be administered in dosages and by techniques well known to those skilled in the medical arts taking into consideration such factors as the age, sex, weight, and condition of the particular subject, and the route of administration.

The DC can be administered prophylactically or therapeutically. In prophylactic administration, the DC can be administered in an amount sufficient to induce a response. In therapeutic applications, the DCs are administered to a subject in need thereof in an amount sufficient to elicit a therapeutic effect. An amount adequate to accomplish this is defined as "therapeutically effective amount." Amounts effective for this use will depend on, e.g., the particular composition of the DC regimen administered, the manner of administration, the stage and severity of the disease, the general state of health of the patient, and the judgment of the prescribing physician. A therapeutically effective amount is also one in which any toxic or detrimental effects of a DC are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a DC, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg. A therapeutically effective amount of a DC may be about $1 \times 10^6$ to about $1 \times 10^{10}$ cells per subject or dose.

The DC can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DC can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The DC can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the DC is administered intravenously, intraarterially, or intraperitoneally to the subject. In some embodiments, the DC is administered to the central nervous system of the subject. In some embodiments, the DC is administered to the subject intravenously.

The DC is administered to a patient in a single dose or in multiple doses. In some embodiments, the DC is administered to the patient bi-weekly.

5. Methods a. Methods of Inducing an Immune Response

Provided herein are methods of inducing an immune response in a patient. The methods may include administering to the patient a DC or vaccine as detailed herein. The vaccine may activate a T cell response, T cell immunity, a B cell response, or a combination thereof. In some embodiments, the DCs as detailed herein may be used as an adjuvant. An adjuvant may increase the immunogenicity of the antigen. The DCs or vaccines as detailed herein may be delivered or administered to a patient to modulate the activity of the patient's immune system and enhance the immune response. The DCs or vaccines as detailed herein may be used to induce immune responses including therapeutic immune responses or prophylactic immune responses. Antibodies and/or killer T cells may be generated that are directed to the antigen.

Also provided herein are methods of treating a disease in a patient. The methods may include administering to the patient a DC or vaccine as detailed herein. The vaccine may activate a T cell response, T cell immunity, a B cell response, or a combination thereof.

The DC or vaccine may be used to treat various diseases, such as, for example, immunity related disease, cancer, infectious disease, neurological disease, Alzheimer's Disease (AD), juvenile diabetes, multiple sclerosis, psoriasis, systemic lupus erythematosus (SLE), and rheumatoid arthritis. In some embodiments, the DC or vaccine is administered to a patient having a disease selected from cancer, autoimmune disease, infectious disease, and neurological disease. In some embodiments, the neurological disease comprises Alzheimer's Disease (AD).

In some embodiments, the vaccine induces an increased immune response compared to a vaccine comprising a mature dendritic cell. In some embodiments, the vaccine induces an immune response similar to a response induced by a vaccine comprising a dendritic cell that is autologous to the patient.

b. Methods of Formulating a Vaccine

Provided herein are methods of formulating a vaccine. The method may include obtaining an immature dendritic cell, contacting the immature dendritic cell with an antigen to form an immature antigen sensitized dendritic cell, and formulating the vaccine comprising the immature antigen sensitized dendritic cell and a pharmaceutically acceptable carrier. In some embodiments, the method further includes killing the immature antigen sensitized dendritic cell. In some embodiments, killing comprises sonication, heat treatment, lyophilization, or a combination thereof. In some embodiments, the method includes sonicating the immature antigen sensitized dendritic cell, collecting the resulting cell debris, and lyophilizing the cell debris into a powder. In some embodiments, the method further includes formulating the lyophilized cell debris or powder into a vaccine.

For example, the method of formulating a vaccine may include any combination of steps selected from collecting blood or bone marrow, isolating the monocytes from the blood or bone marrow and differentiating the DCs, contacting the DCs with an antigen to form an immature antigen sensitized dendritic cell, harvesting or collecting the immature antigen sensitized dendritic cell, sonicating the immature antigen sensitized dendritic cell to kill the cell and make cell debris, collecting the cell debris, lyophilizing the cell debris, formulating the cell debris into a vaccine. The vaccine may be administered to a patient, as detailed above.

6. EXAMPLES

Example 1

Materials and Methods

Mouse bone marrow derived dendritic cell preparation: Mouse bone marrow cells were harvested from 10 week-old BALB/c mice or C57/BL6 mice and differentiated with IL4 and GM-CSF. Half of the prepared dendritic cells were sensitized with the antigen (immature) and the other half was stimulated with TNFα, IL6, and IL1α (matured first), then antigen was loaded to the matured dendritic cells. Early maturation of DCs was conducted at day 4 after differentiation by adding TNFα, IL6, and IL1α for three days and then antigen was loaded. DCs were harvested at day 10. The regular maturation was conducted at day 7 after being differentiated with TNFα, IL6, and IL1α, and then antigen was loaded after three days, and then DCs were harvested at day 12.

Human monocyte derived dendritic cell preparation: Human buffycoat was ordered from the Florida blood bank, and monocytes were isolated by using the standard reported protocol (Pandha H. S., et al. *BJU Int.* 2004, 94, 412-418). Immature dendritic cells and mature dendritic cells were prepared as the mouse dendritic cell preparation.

Peptide preparation: All peptides were ordered from Biomer Technology Inc. (CA, USA) and then reconstituted with HFIP, and then aliquoted into 100 µg/vial. Peptides then were stored at −80° C. after being dried by speedVac.

Immunization and monitor of response: Immature and mature dendritic cells were used as a vaccine to inject BALB/c mice and C57/BL6 mice at bi-weekly intervals. Both the whole live cell and the cell lysates of immature and mature dendritic cells were used to vaccinate BALB/c mice and C57/BL6 mice at bi-weekly intervals.

Sample collection and processing: Blood samples were taken by the submandibular vein punctuation for pre-immunization and 10 days after the second immunization. The plasma was isolated by centrifugation, and the blood cells were used for cellular staining using the selected markers.

Flow cytometry assay: A panel of dendritic cell maturation markers (CD40, CD80, CD86, MHC-II, and CD11c) were used to monitor and track the maturation of dendritic cells. Cells were counted using a flow cytometer at designated time points.

Whole, live dendritic cell and cell lysate preparation: Dendritic cells (both mature and immature samples) were prepared and stained with the selected DC markers as described (MHCII, CD11c, CD80, CD83, and CD86). Half of the prepared cells were submitted for sonication to destroy the cell. Both the whole live cell and the cell lysates were submitted to a flow cytometer for size determination and to confirm the disruption of the cells.

Antibody detection: ELISA assays were used to detect antibody production, and epitope mapping was also conducted with ELISA assay.

Ig-isotyping assay: Luminex assay was used to detected plasma IgA, IgD, IgE, and IgG1, IgG2a, IgG2b, and IgG3 (Cat #Millipore USA)

Cytokine expression profile detection: Luminex multiplex assay was used to detect a panel of cytokines (IL1, IL2, IL4, IL6, IL10, IL12, IFNr, and TNFa) from both pre-vaccine plasma and post-vaccine plasma by following the instructions in the manual provided by the company.

Example 2

Figure 1B:
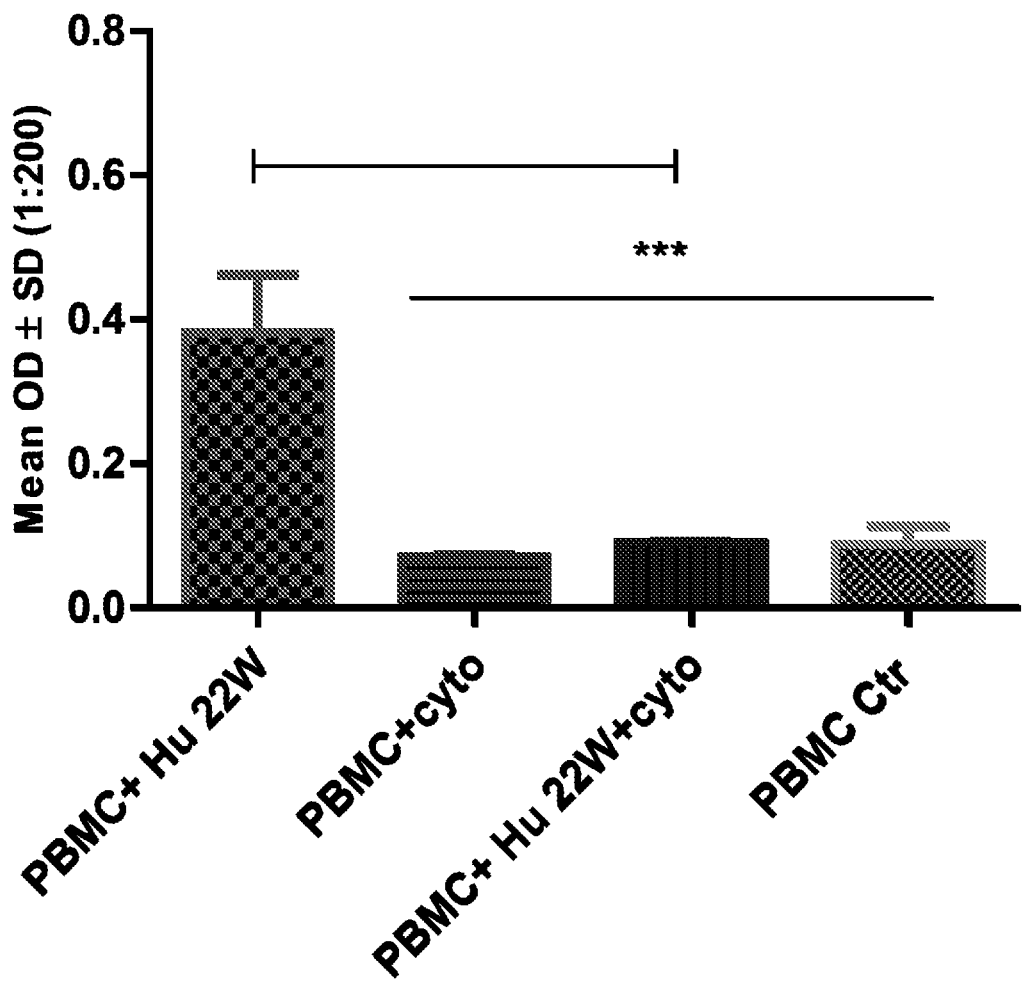

Human Mononuclear Cell Differentiated Immature Dendritic Cells have Better Function in Inducing an Immunoresponse than Mature Dendritic Cells Antibody response, Ig immunotype, T cell response, and homing of various dendritic cell samples were examined. Results are shown in FIG. 1A and FIG. 1B, which are graphs showing the flow cytometry results of dendritic cell maturation and immune response of peptide sensitized mature and immature dendritic cells as a vaccine. FIG. 1A shows the flow cytometry result of dendritic cell maturation. Cell surface markers used were CD80, CD86, MHCII, and CD11b. Cytokines used for maturation were human Ma, IL6, and TNFα. FIG. 1B is the ELISA result for Anti-Aβ antibody detection post vaccination with peptide (Aβ) sensitized immature dendritic cells (labeled as "PBMC+Hu 22W"), peptide sensitized matured dendritic cells (labeled as "PBMC+Hu 22W+cyto"). matured dendritic cells (labeled as "PBMC+cyto"), and immature dendritic cells (labeled as "PBMC Ctr"). As shown, when used as a vaccine only the peptide sensitized immature dendritic cells induced an antibody response, while the mature dendritic cells failed to induce an antibody response.

Example 3

Dendritic Cell Homing May Just be a Natural Process, but it is not a Required Procedure for Dendritic Cell Function Dendritic cell homing was examined using cells expressing GFP.

Figure 2A:
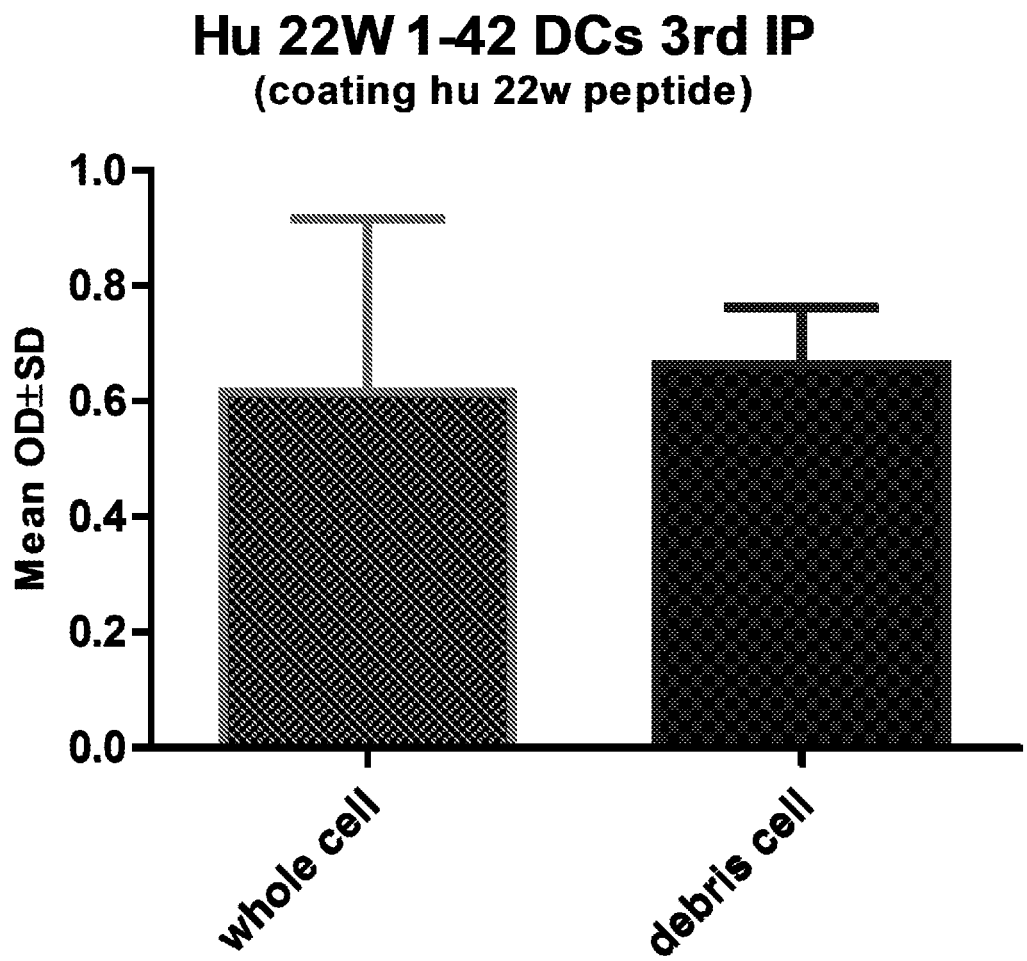
FIG. 2A, FIG. 2B, and FIG. 2C are graphs showing the antibody response and epitope mapping result after vaccination.
Figure 2B:
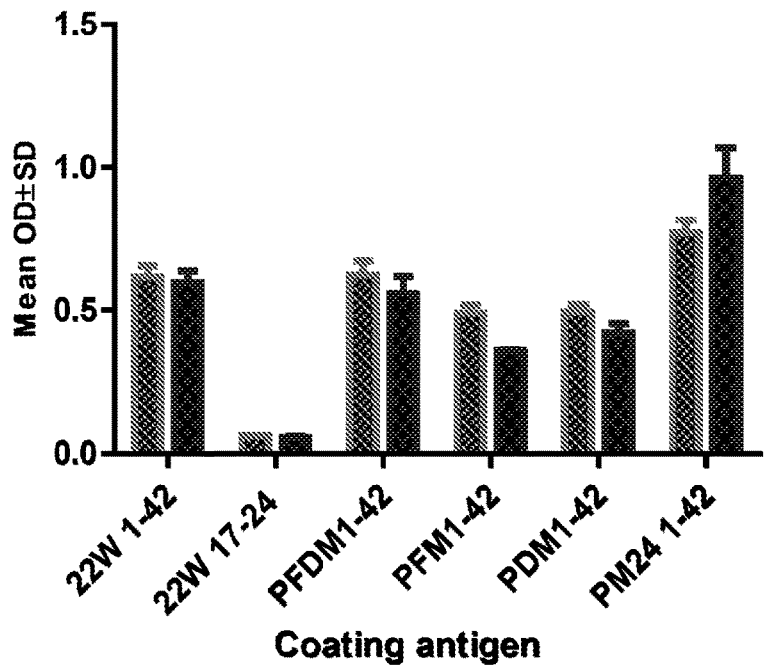
Figure 2B:
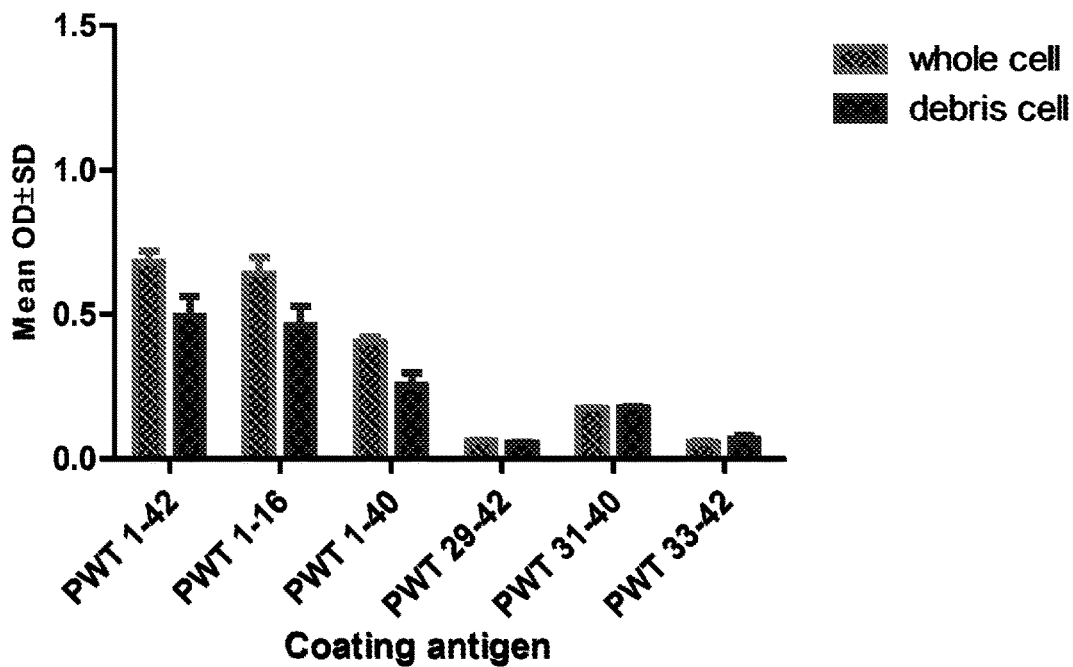
Figure 2C:
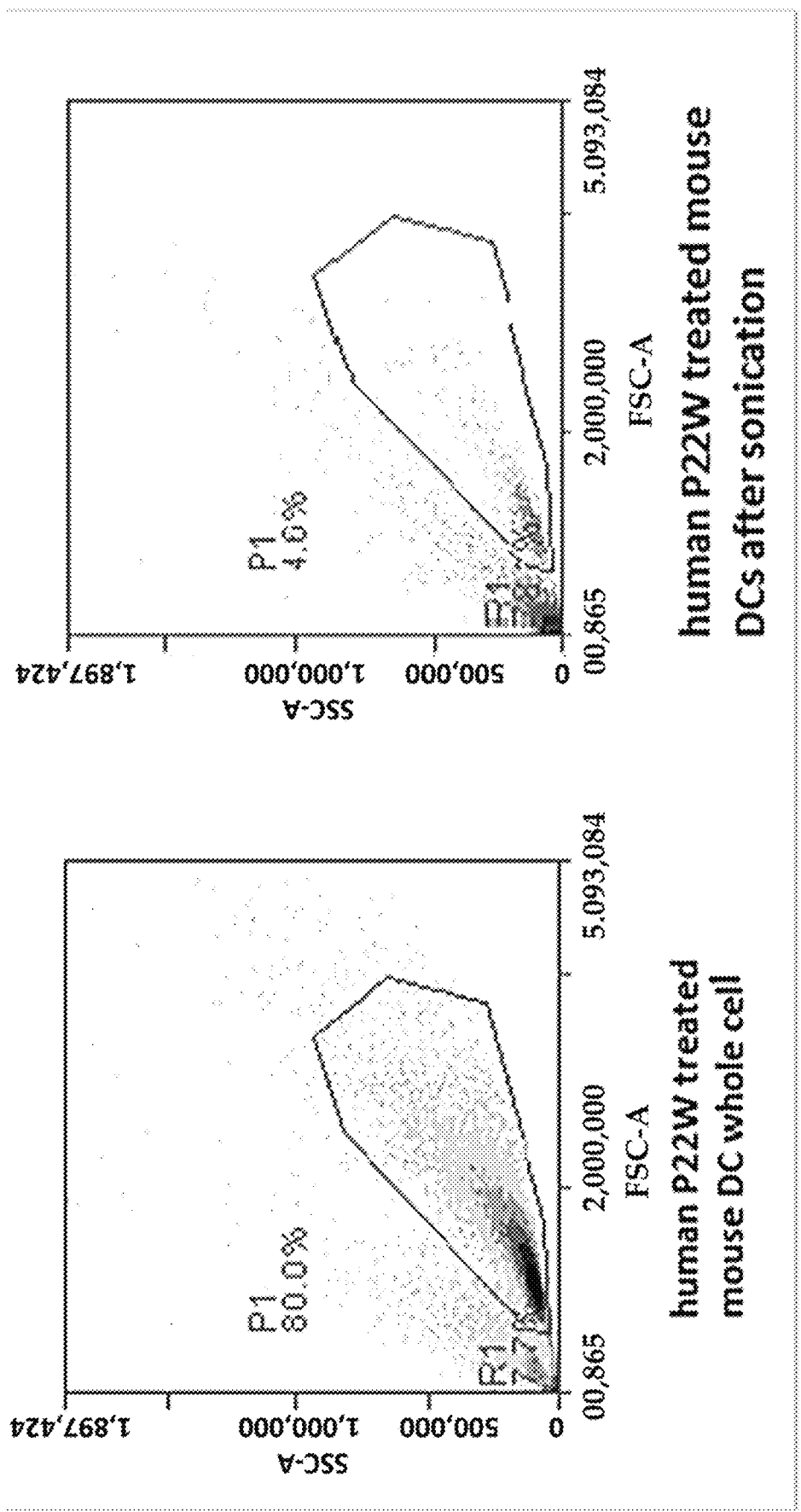
Figure 3A:
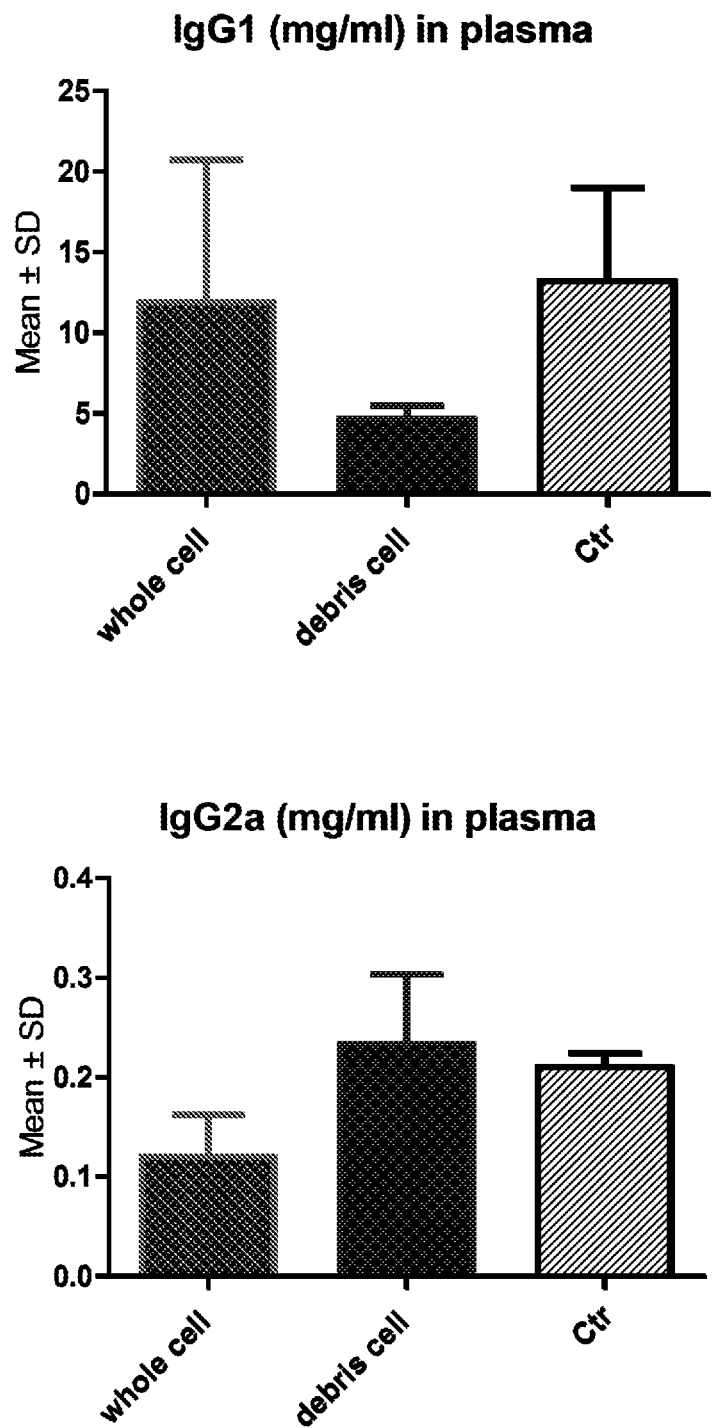
FIG. 3A, FIG. 3B, FIG. 3C, FIG. 3D, FIG. 3E, and FIG. 3F are graphs showing results from isotyping and the cytokine expression profile post vaccination. The blood was collected 10 days after the third vaccination, and the plasma was used to check the Ig-isotyping and cytokine expression profile by using Luminex multiplex assay. There was no increase in inflammatory cytokine post-vaccination between whole cell and cell debris. The cell debris induced a Th1 response after the third vaccination, but this response diminished after the fourth vaccination (data not shown).
Figure 3B:
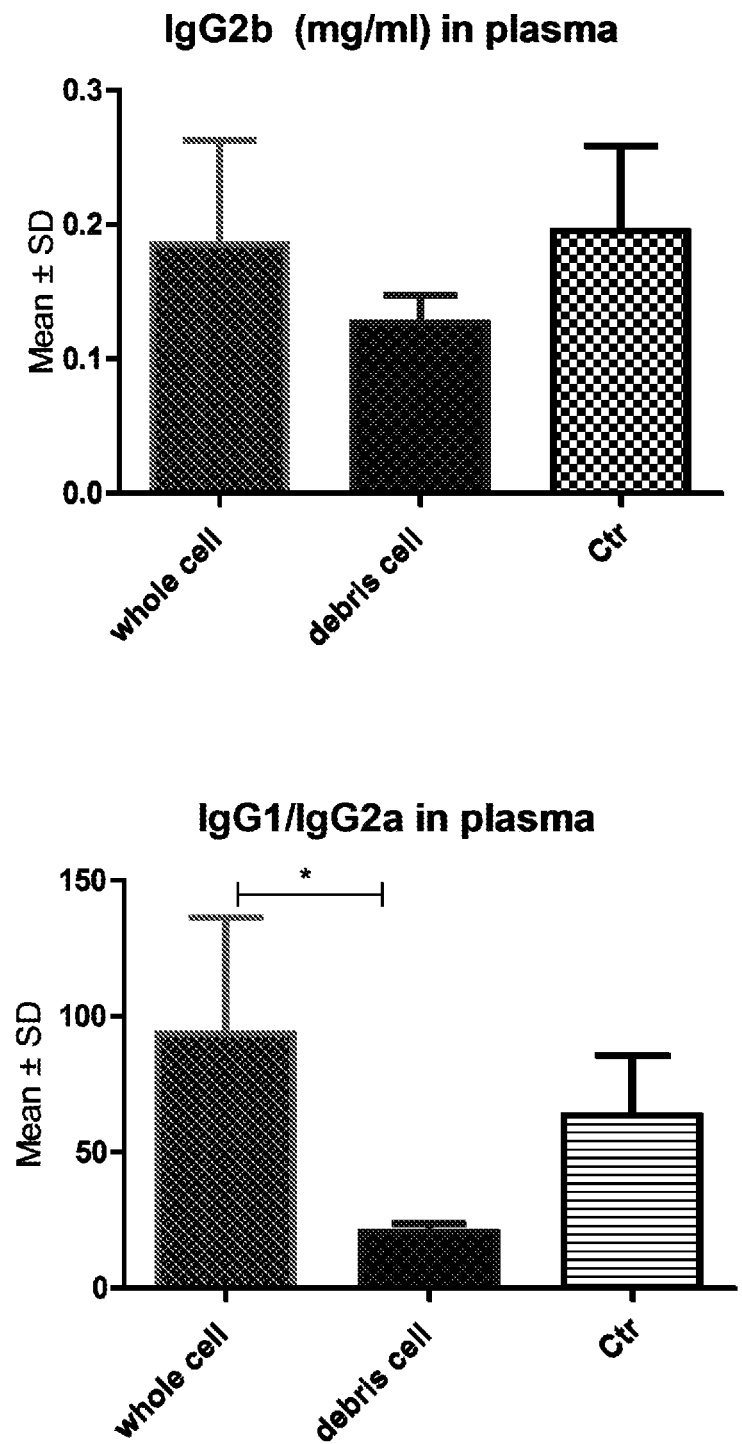
Figure 3C:
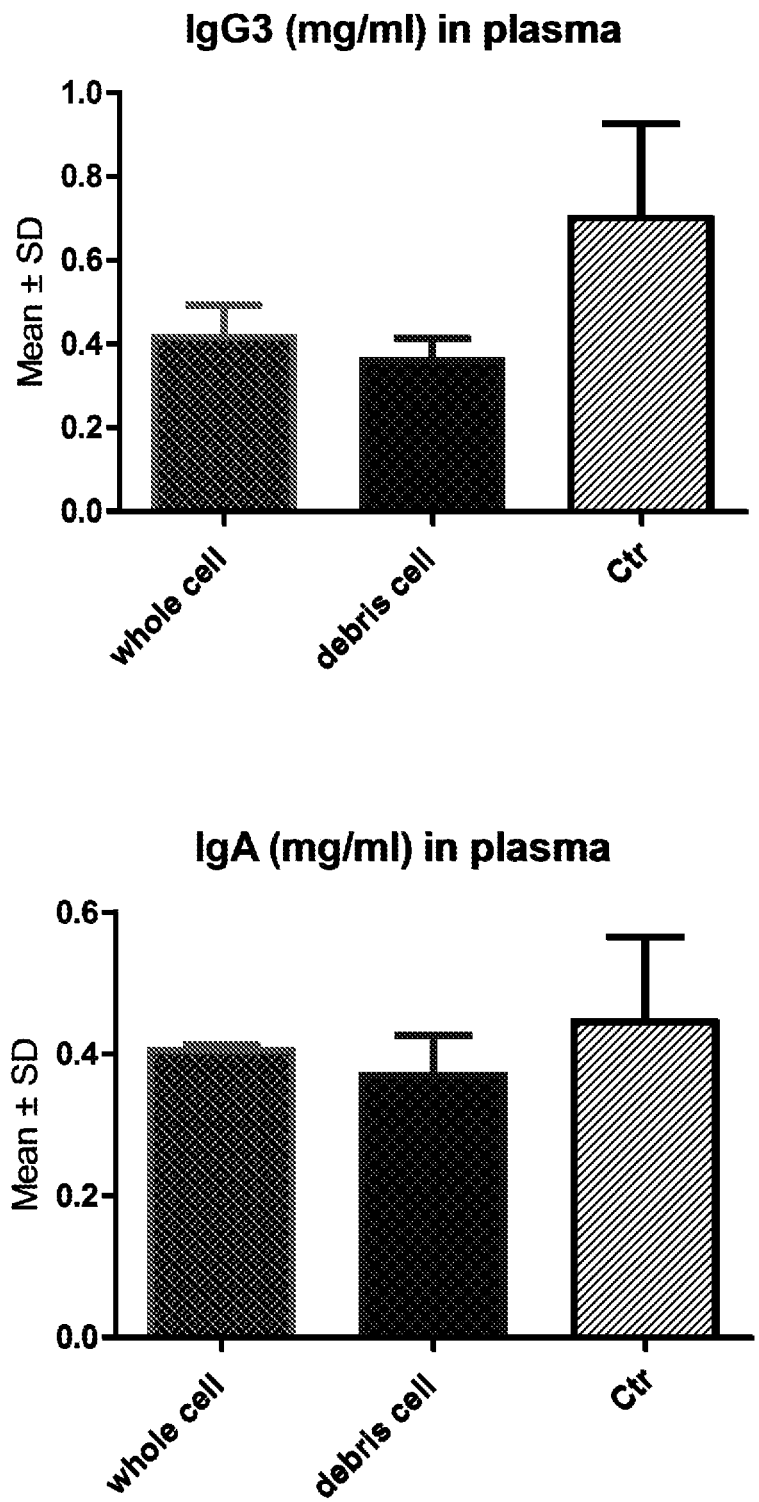
Figure 3D:
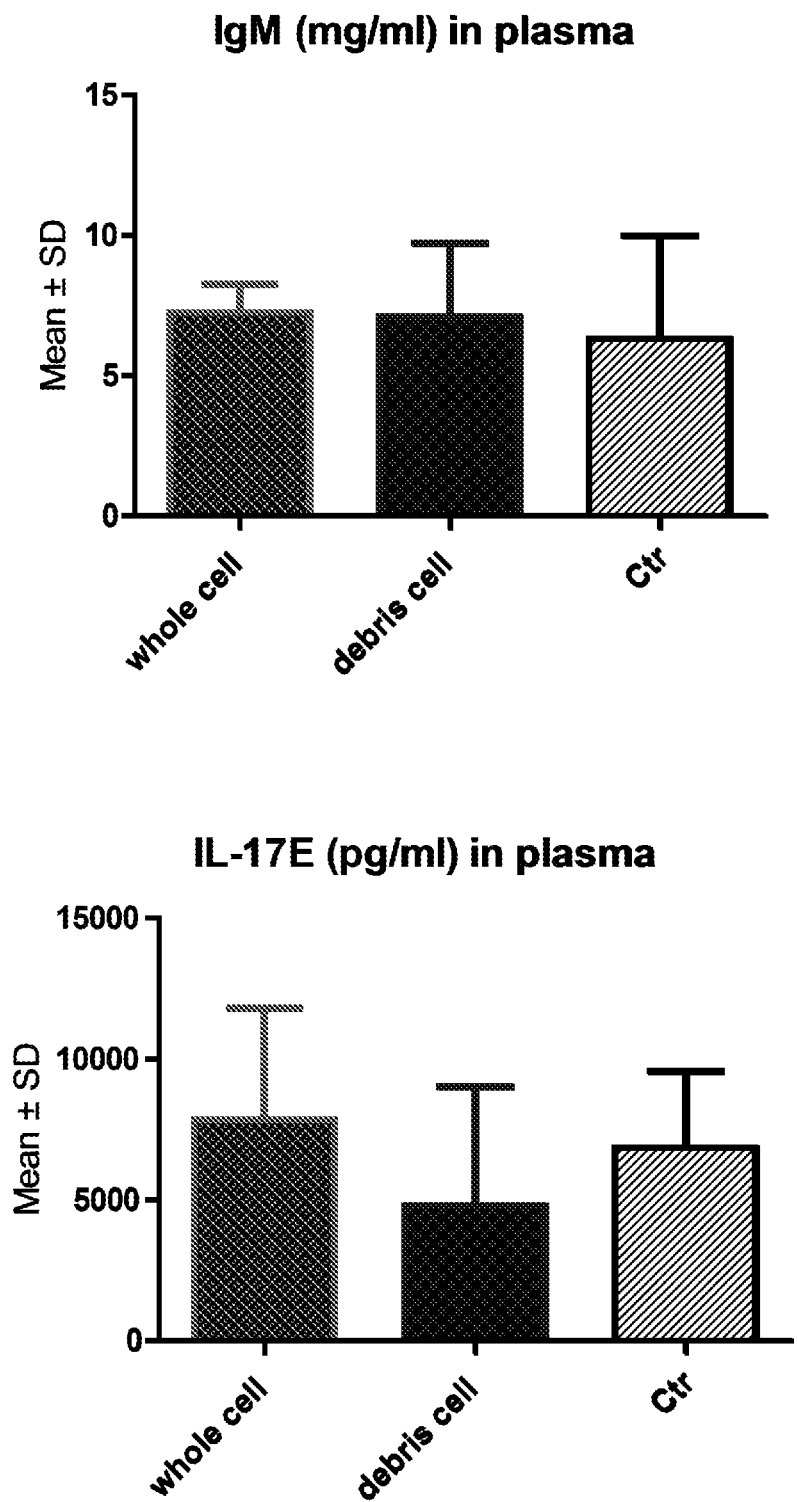
Figure 3E:
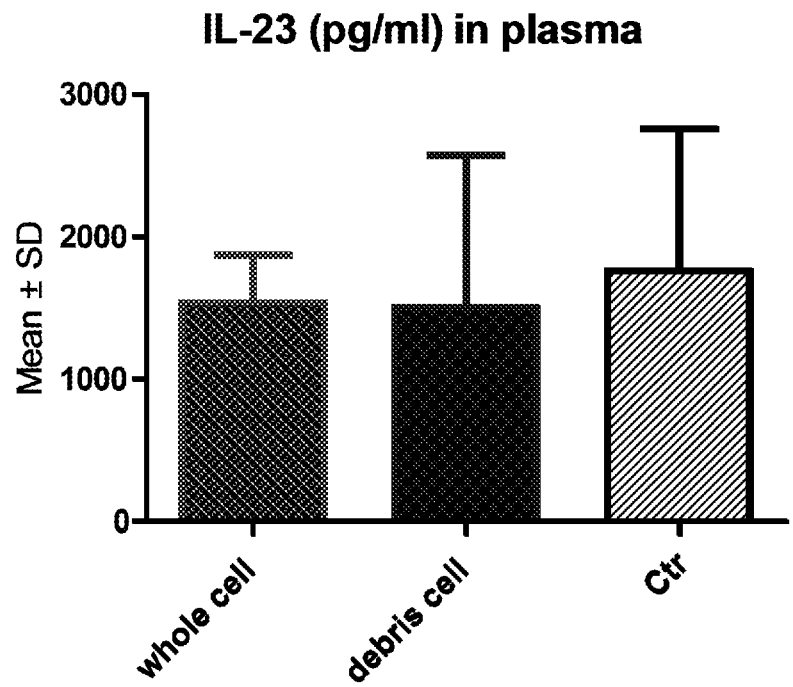
Figure 3E:
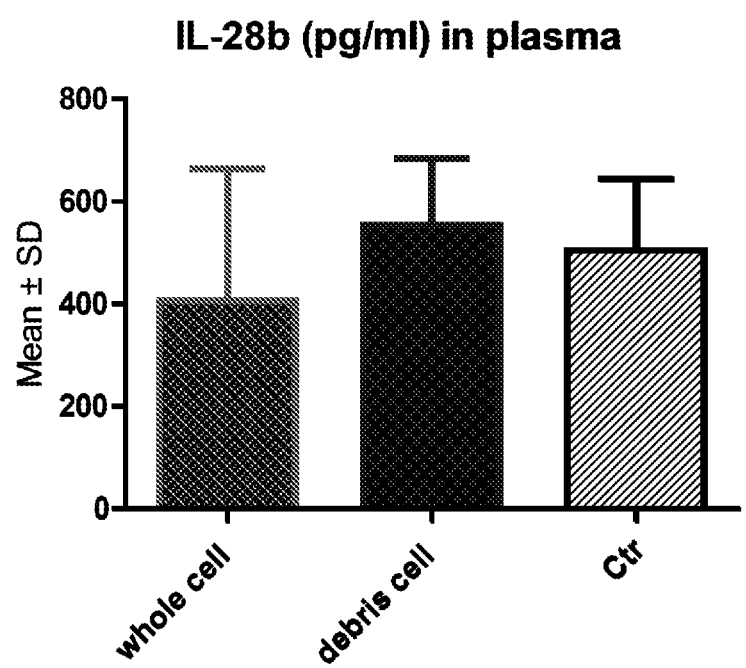
Figure 3F:
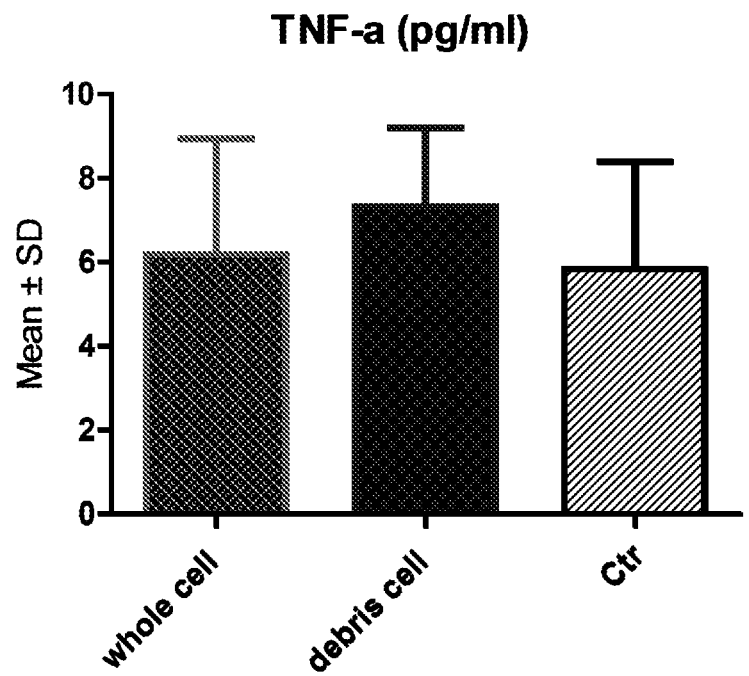
Figure 3F:
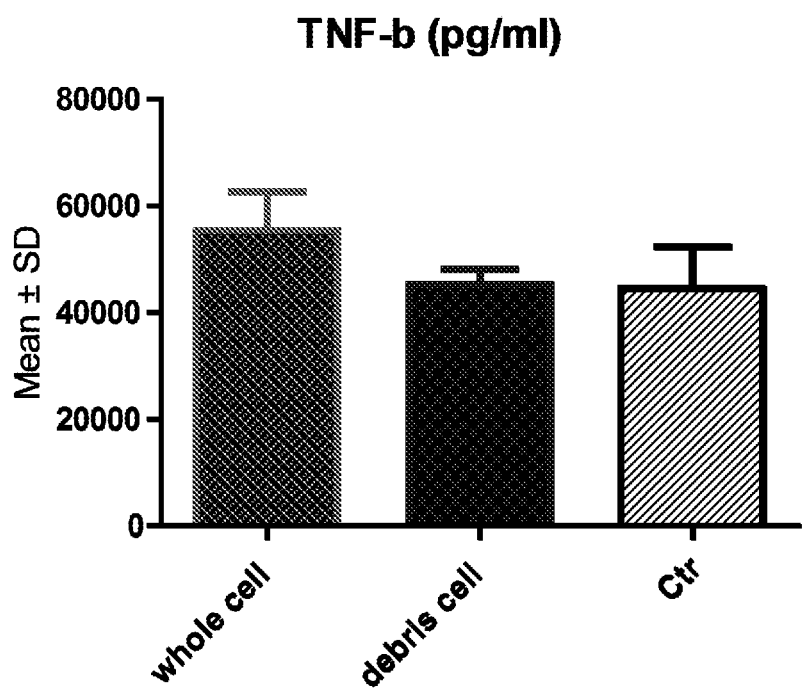

Results are shown in FIG. 2A, FIG. 2B, and FIG. 2C, as the antibody response and epitope mapping result after vaccination. FIG. 2A is the antibody response against human Aβ42 with a mutation at the 22 amino acid (22W) after 2 vaccinations with either the whole cell peptide sensitized dendritic cells or the same cell batch lysed by sonication for 10 seconds. The dendritic cells were prepared from 2 month old BALB/c mice bone marrow by following the method detailed in Cao et al. (*J. Neuroimmunol.* 2008, 200, 1-10). Then $1 \times 10^6$ whole cells or lysed cells were injected into 2 month old BALB/c mice, and the mice were boosted two weeks later with the same vaccine. Blood was collected 10 days after the second vaccination. Two mice (n=2) were injected with whole cells by intraperitoneal injection, and three mice were injected with cell debris (the antigen sensitized, n=3). Both the whole cell and lysed cell debris induced high antibody response, and as seen in the top panel graph, there was no significant difference between the two groups (P>0.05). FIG. 2B is the epitope mapping against all mutant peptides and fragments of Aβ. We selected one plasma from each group and tested the antibody binding to different peptides. As shown in the graph, there was no difference between the two sera against all detected peptides, so the epitope remained the same. There was no epitope change between whole cell and cell debris. The graph on the right is the epitope mapping against wild-type Aβ peptide fragments tested to the same two anti-sera shown in the middle graph. Again, there was no difference between the two anti-sera. Both the whole cell and the lysed cell (debris) induced an antibody response. FIG. 2C is the flow cytometry result of whole cells versus sonicated cells. The particle size was much smaller than the whole cell, which indicated that the majority of cells were disrupted by sonication.

Shown in FIG. 3A, FIG. 3B, FIG. 3C, FIG. 3D, FIG. 3E, and FIG. 3F are graphs showing isotyping and cytokine expression profile post vaccination. The blood was collected 10 days after the third vaccination, and the plasma was used to check the Ig-isotyping and cytokine expression profile using Luminex multiplex assay. No inflammation cytokines increased post-vaccination in either the whole cell or the cell debris. The cell debris did induce a Th1 response after the third vaccination, but this response diminished after the fourth vaccination (data not shown).

Figure 4A:
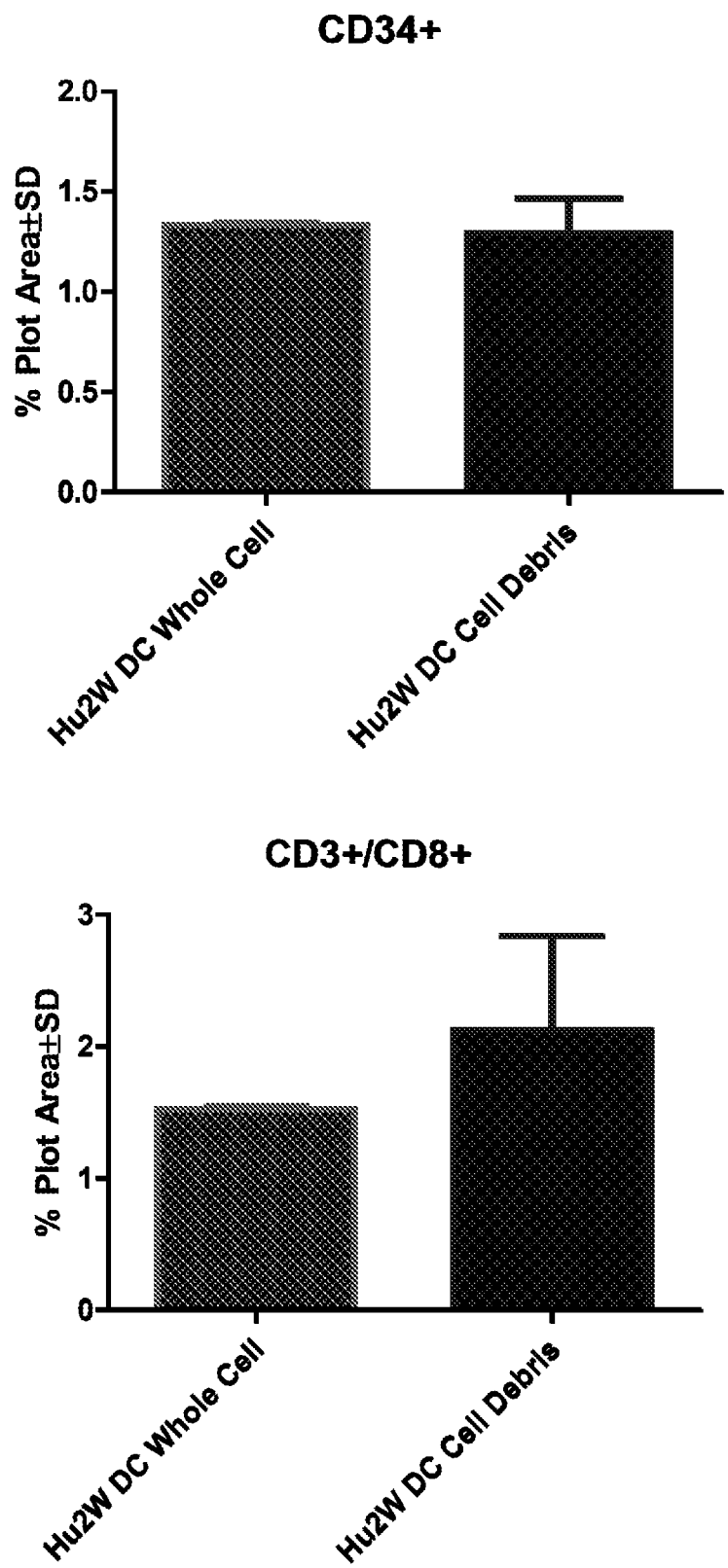
FIG. 4A, FIG. 4B, and FIG. 4C are graphs showing the flow result of lymphocytes from post-vaccinated blood. We analyzed stem cells, CD4, CD8 dendritic cells, and memory B cell populations, and there was no difference in results from the whole cell and cell debris. The results indicated that there was no difference in the immune response between these two vaccinations.
Figure 4B:
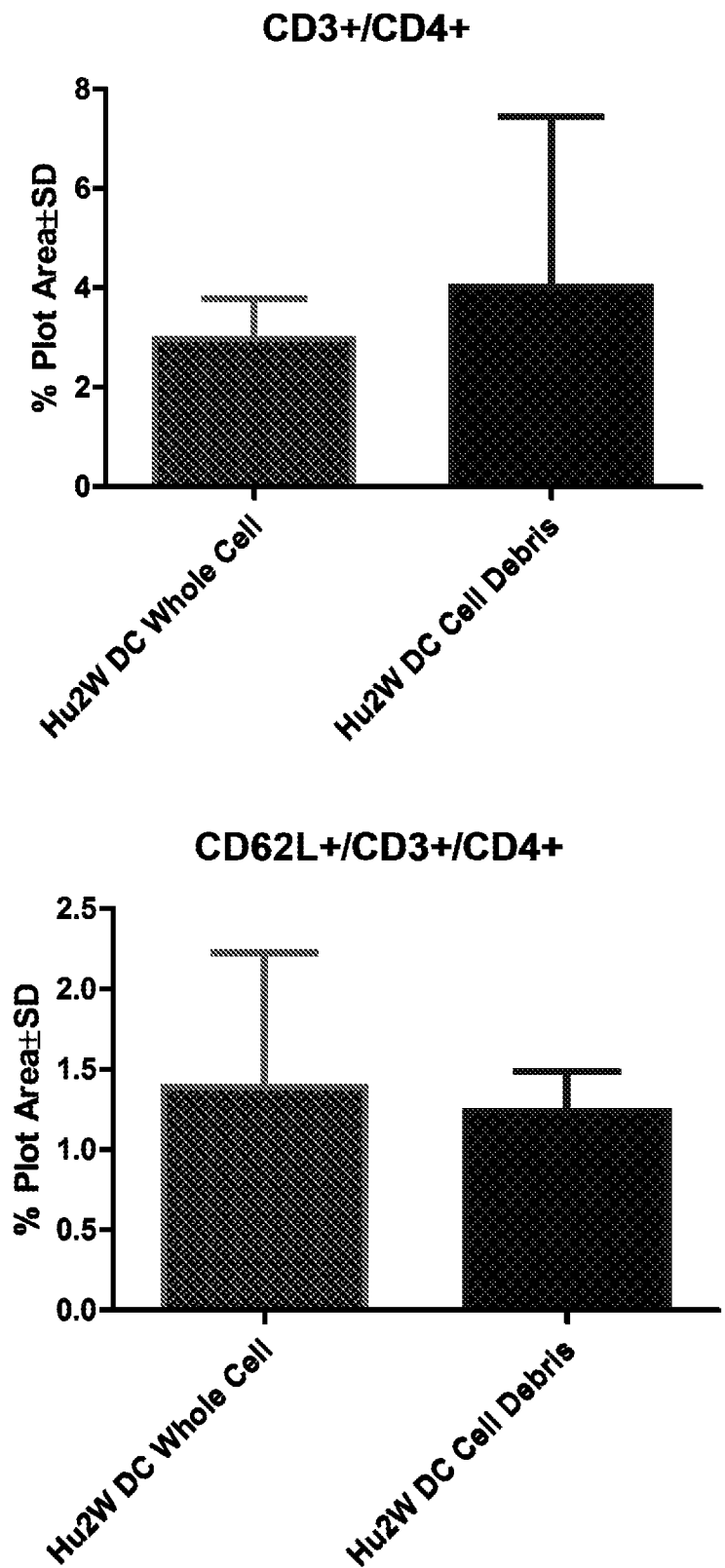
Figure 4C:
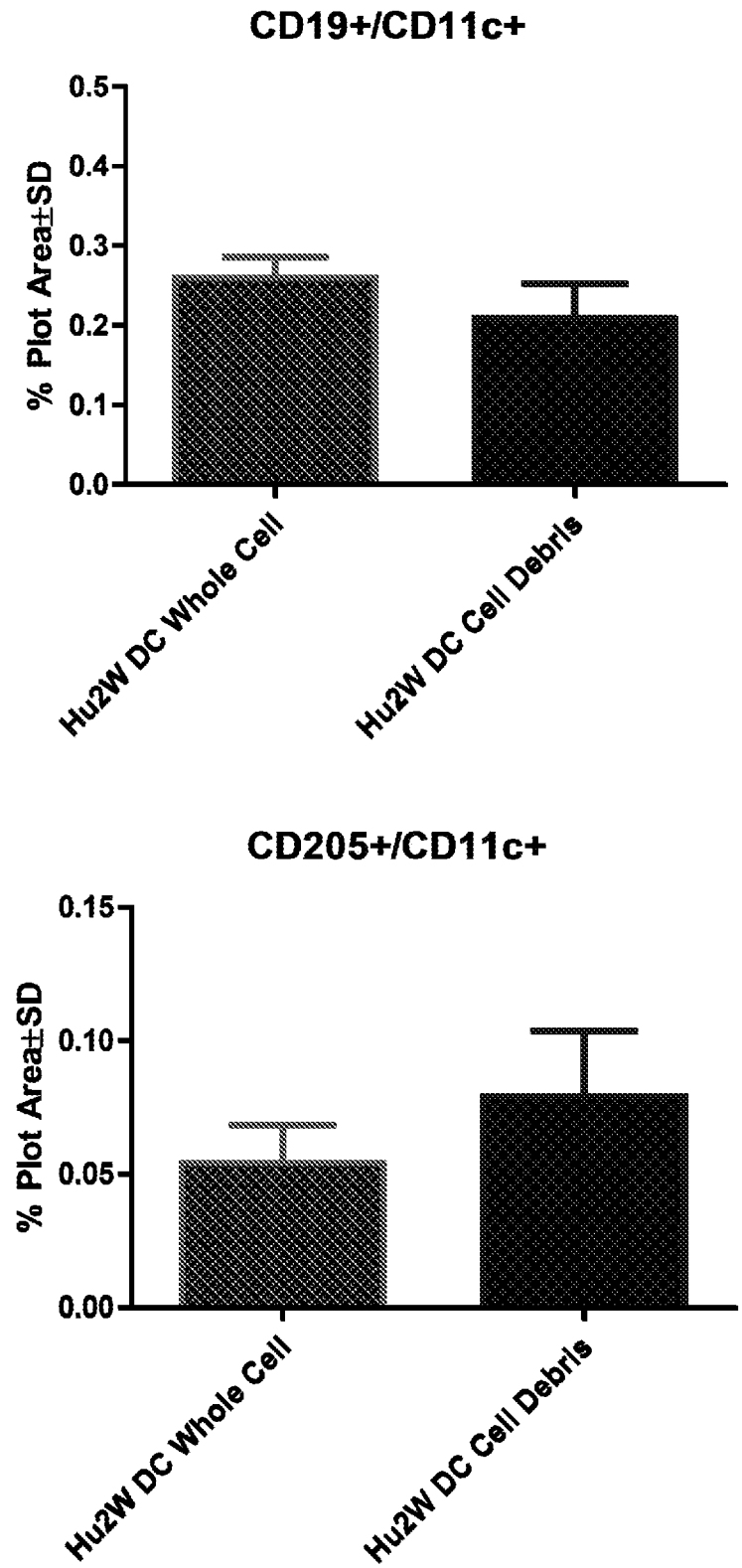

Shown in FIG. 4A, FIG. 4B, and FIG. 4C are graphs showing the cytometry result of lymphocytes from post-vaccinated blood. Stem cells, CD4, CD8 dendritic cells, and memory B cell populations were analyzed. No difference was found between the whole cell and cell debris samples, indicating that there was no difference in the immunoresponse elicited by the two different vaccinations.

The results indicated that whole (live cells) and cell lysates (dead cells) have the same function (antibody response, immunotype, homing is not necessary, and T cell response).

Example 4

DCs Induce Immunoresponses

Mature dendritic cells are less potent in antigen phagocytosis and antigen presentation than immature dendritic cells. Mature dendritic cells have begun the apoptosis signaling cascade, so mature DCs may have relatively shorter life spans and less activity than immature DCs (Winzler C., et al. *J. Exp. Med.* 1997, 185, 317-328; Rescigno M., et al. *J. Exp. Med.* 2000, 192, 1661-1668).

Figure 5A:
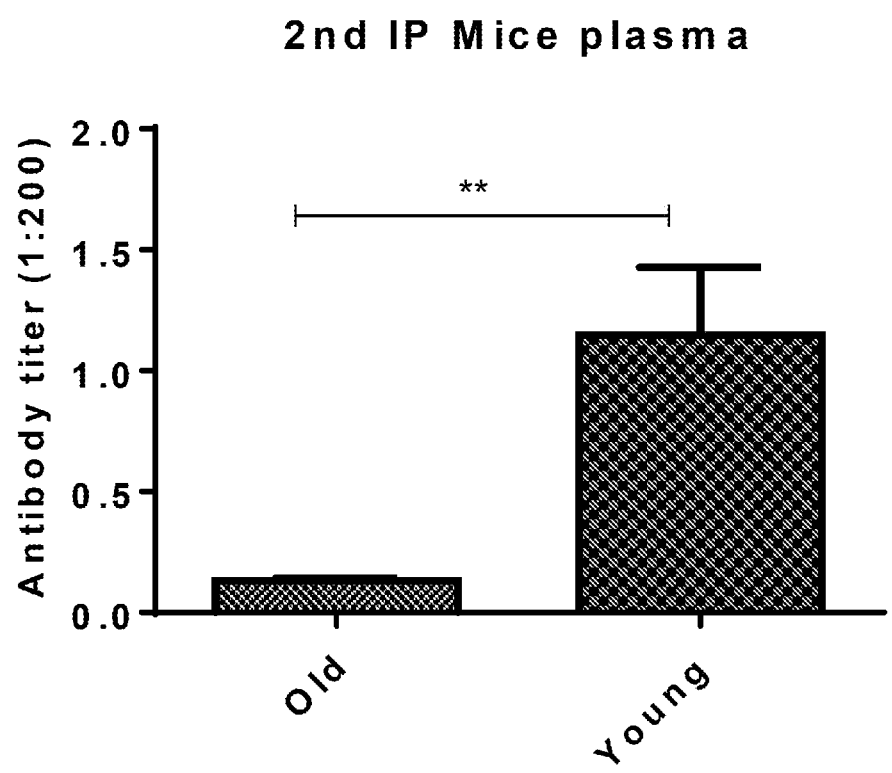
FIG. 5A, FIG. 5B, FIG. 5C, and FIG. 5D are results showing the immunoresponse induced by DCs.
Figure 5B:
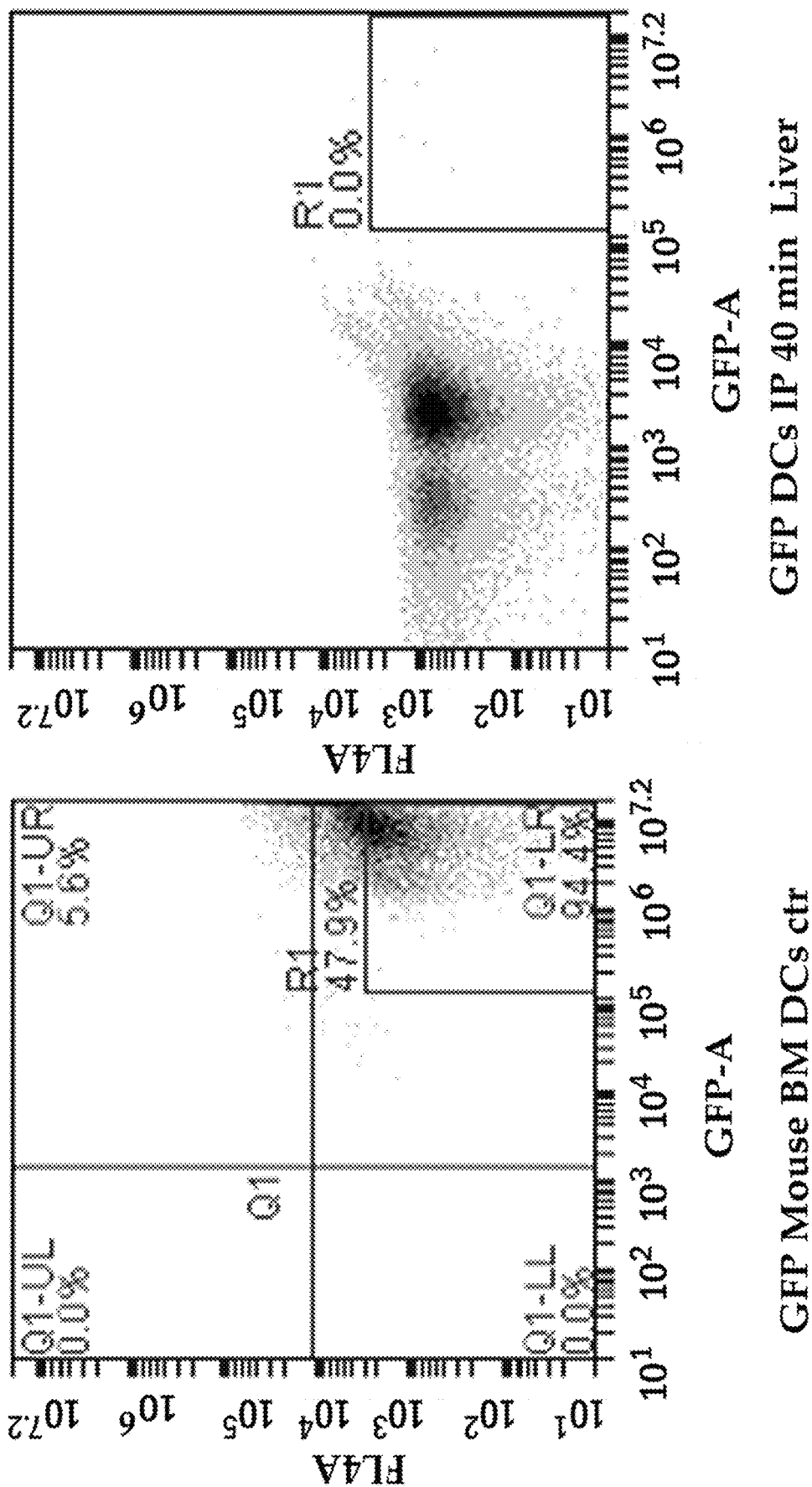
Figure 5C:
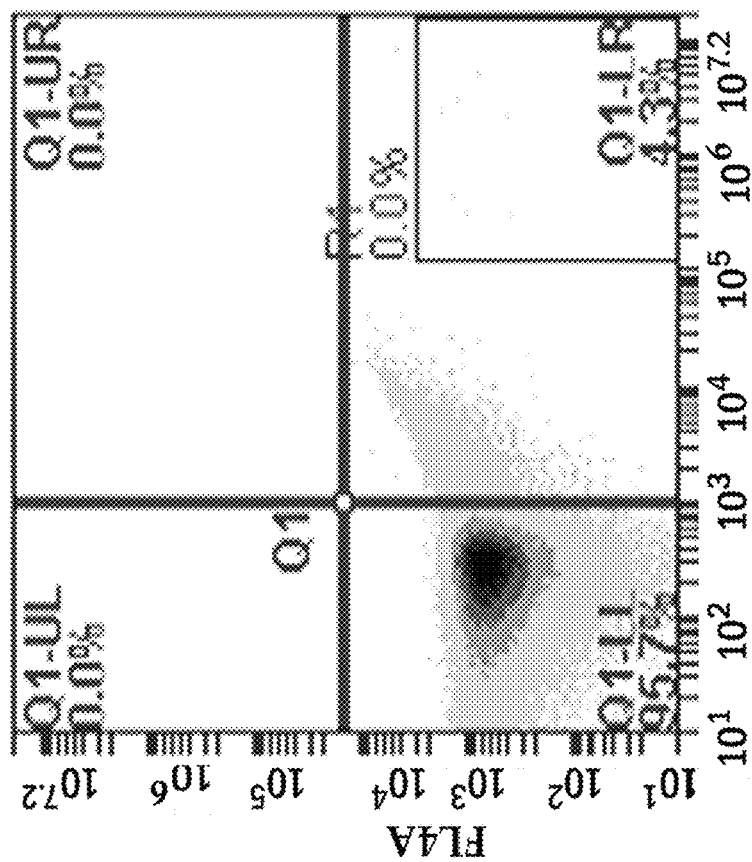
Figure 5C:
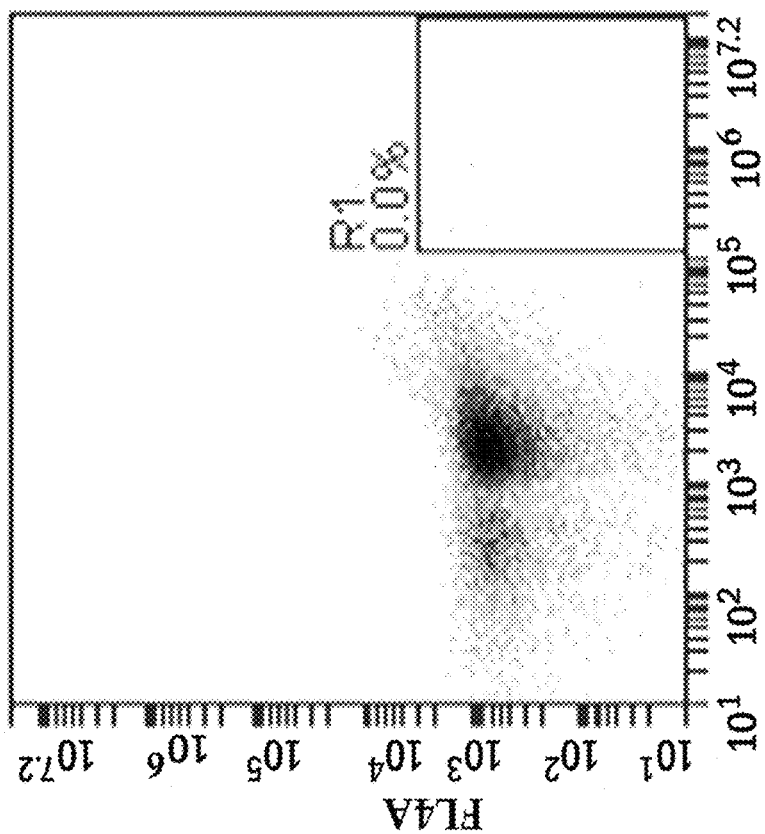
Figure 5D:
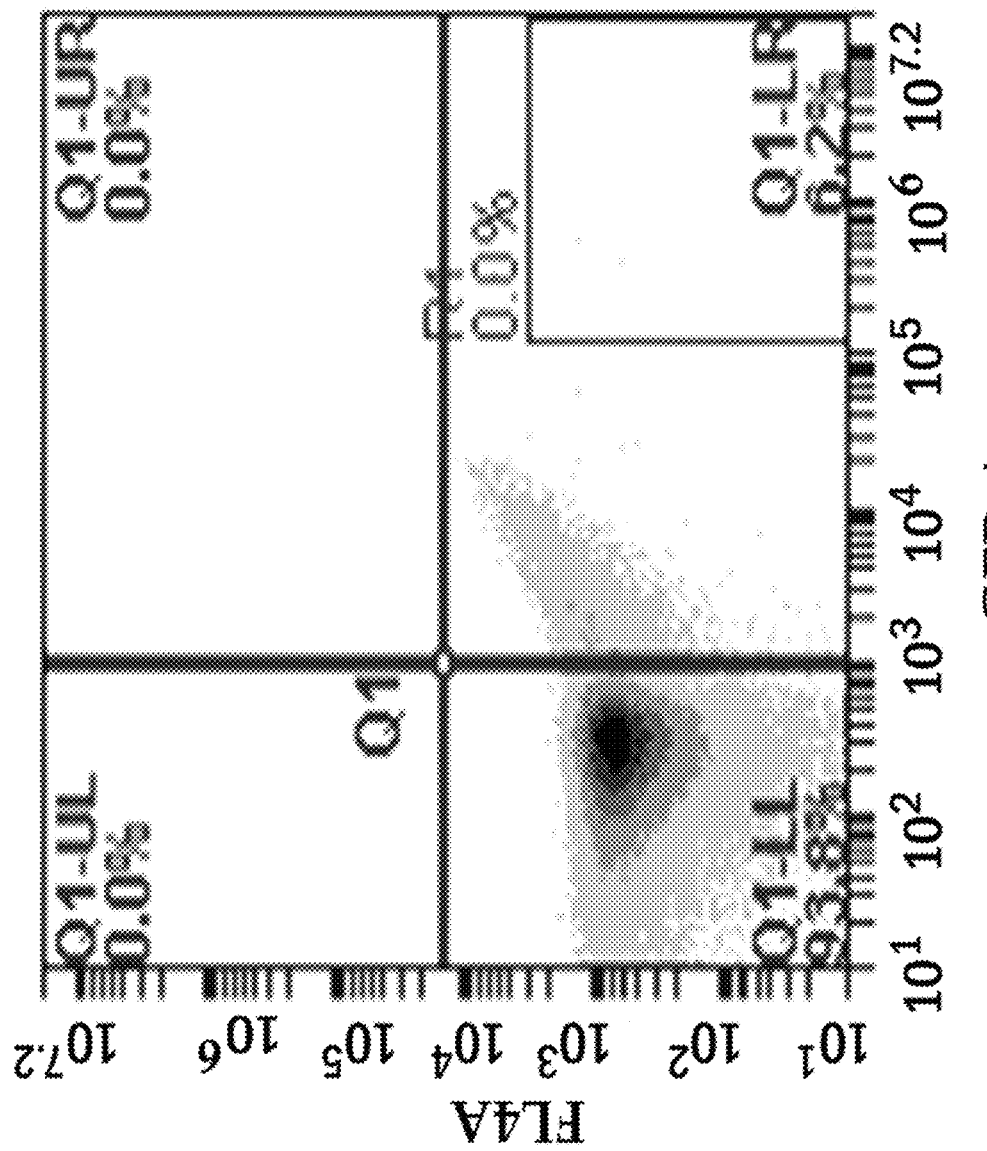

The amyloid beta (Aβ) peptide with a mutation in the T cell epitope is important for successfully sensitizing DCs and can elicit antibody responses in mice. There were no differences between tail vein injection and intraperitoneal injection in inducing immunoresponses. We gave peptide sensitized DCs from BALB/c mice to C57/B6 mice for up to 5 injections and discovered that there was no abnormal response in either the peripheral or central immune systems. We also compared the immunization results from mature versus immature DCs sensitized with mutant peptide, and the results clearly demonstrated that immature DCs have much better immunoresponse than mature DCs (see FIG. 1B]). Although other research groups use or have used live DCs as treatment, and without being limited by theory, we believe all signals may be fully equipped in vitro, and it does not matter whether DCs are alive or dead. There were no differences between live DCs and dead DCs in inducing immunoresponse in a mouse mode (see FIG. 2A, FIG. 2B, and FIG. 2C). The effect of delivering human DCs to mice was examined, and the cross-species recipient injection of antigen sensitized DCs also showed a successful immunoresponse without any adverse effects (see FIG. 3A-FIG. 3F). Peptide sensitized DCs can induce immunoresponse in old mice. DCs harvested from young mice were injected into old and young mice, and it was discovered that young mice had a significantly better immunoresponse than old mice (see FIG. 5A). To examine DC homing to immune organs (spleen and lymph nodes) after injection, we generated DCs from GFP mice, injected them into C57/B6, and collected blood and spleens at different time points. Not many GFP cells were found (see FIG. 5B, FIG. 5C, and FIG. 5D). These results implied that DC homing to spleen and lymph nodes may be a natural procedure, but it may not be a necessary step in DC immunomodulatory function.

A novel procedure for making an antigen sensitized immature dendritic cell vaccine has been developed that is better than conventional methods and vaccines with mature DCs. An exogenous DC vaccine may be used in therapeutic applications, making it possible, for example, to use DCs from exogenous younger donors for more effective treatment. Being able to use dead DCs, lysed DCs, or DC debris, for example, rather than live DCs may make development of the vaccines cheaper, more cost-effective, and more therapeutically effective, and facilitate easier transport and greater availability.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A vaccine for a patient, the vaccine comprising an antigen sensitized immature dendritic cell, wherein the dendritic cell is exogenous to the patient.

Clause 2. The vaccine of clause 1, wherein the dendritic cell is from a subject of the same species as the patient.

Clause 3. The vaccine of clause 2, wherein the dendritic cell is from a subject that is younger than the patient and of the same species as the patient.

Clause 4. The vaccine of clause 1, wherein the dendritic cell is from a subject of a different species than the patient.

Clause 5. The vaccine of any one of the above clauses, wherein the dendritic cell is dead.

Clause 6. The vaccine of clause 5, wherein the dendritic cell was killed by sonication, heat treatment, lyophilization, or a combination thereof.

Clause 7. The vaccine of an clause 5, wherein the dendritic cell is a lysed cell or a portion thereof.

Clause 8. The vaccine of any one of the above clauses, wherein the dendritic cell has not been matured by stimulation with cytokines selected from TNFα, IL6, and IL1α.

Clause 9. The vaccine of any one of the above clauses, wherein the vaccine induces an increased immune response compared to a vaccine comprising a mature dendritic cell.

Clause 10. The vaccine of any one of the above clauses, wherein the vaccine induces an immune response similar to a response induced by a vaccine comprising a dendritic cell that is autologous to the patient.

Clause 11. The vaccine of any one of the above clauses, wherein the dendritic cell is antigen sensitized by contacting with the antigen.

Clause 12. The vaccine of clause 11, wherein the dendritic cell is contacted with the antigen in vitro.

Clause 13. The vaccine of any one of the above clauses, wherein the antigen comprises a peptide, a protein, a carbohydrate, a lipid, or a combination thereof.

Clause 14. The vaccine of clause 13, wherein the antigen comprises a peptide.

Clause 15. The vaccine of any one of the above clauses, wherein the dendritic cell is derived from blood or bone marrow.

Clause 16. The vaccine of any one of the above clauses, wherein the dendritic cell is a monocyte-derived immature dendritic cell.

Clause 17. A method of inducing an immune response in a patient, the method comprising administering to the patient a vaccine according to any one of clauses 1-16.

Clause 18. The method of clause 17, wherein the vaccine activates a T cell response, T cell immunity, a B cell response, or a combination thereof.

Clause 19. The method of clause 17 or 18, wherein the vaccine is administered to the patient in multiple doses.

Clause 20. The method of clause 19, wherein the vaccine is administered to the patient bi-weekly.

Clause 21. The method of any one of clauses 17-20, wherein the patient has a disease selected from cancer, autoimmune disease, infectious disease, and neurological disease.

Clause 22. The method of clause 21, wherein the neurological disease comprises Alzheimer's Disease (AD).

Clause 23. A method of formulating a vaccine, the method comprising obtaining an immature dendritic cell; contacting the immature dendritic cell with an antigen to form an immature antigen sensitized dendritic cell; and formulating the vaccine comprising the immature antigen sensitized dendritic cell and a pharmaceutically acceptable carrier.

Clause 24. The method of clause 23, further comprising killing the immature antigen sensitized dendritic cell.

Clause 25. The method of clause 24, wherein killing comprises sonication, heat treatment, lyophilization, or a combination thereof.

Clause 26. The method of any one of clauses 23-25, wherein the dendritic cell is derived from blood or bone marrow.

Clause 27. The method of clause 26, wherein the dendritic cell is a monocyte-derived immature dendritic cell.

The invention claimed is:

1. A vaccine for a patient, comprising an antigen sensitized immature dendritic cell, wherein the dendritic cell is exogenous to the patient, and wherein the dendritic cell is dead.

2. The vaccine of claim 1, wherein the dendritic cell is from a subject of the same species as the patient.

3. The vaccine of claim 2, wherein the dendritic cell is from a subject that is younger than the patient.

4. The vaccine of claim 1, wherein the dendritic cell has not been matured by stimulation with cytokines selected from TNFα, IL6 and IL1α.

5. The vaccine of claim 1, wherein the vaccine induces an increased immune response compared to a vaccine comprising a mature dentritic cell.

6. The vaccine of claim 1, wherein the vaccine induces an immune response about the same as the response induced by a vaccine comprising a dentritic cell that is autologous to the patient.

7. The vaccine of claim 1, wherein the antigen comprises a peptide, a protein, a carbohydrate, a lipid, or a combination thereof.

8. The vaccine of claim 7, wherein the antigen is a peptide.

9. The vaccine of claim 8, wherein the peptide comprises a human Aβ42 with a mutation at the 22 amino acid (22W).

10. The vaccine of claim 1, wherein the dentritic cell is derived from blood or bone marrow.

11. The vaccine of claim 10, wherein the dentritic cell is a monocyte-derivated immature dendritic cell.

12. A method of inducing an immune response in a patient, the method comprising administering to the patient the vaccine of claim 1.

13. The method of of claim 12, wherein administration of the vaccine comprises activating a T cell response, T cell immunity, a B cell response, or a combination thereof.

14. The method of of claim 12, wherein the vaccine is administered to the patient in multiple doses.

15. The method of of claim 14, wherein the vaccine is administered to the patient bi-weekly.

16. The method of of claim 12, wherein the patient has a disease selected from cancer, autoimmune disease, infectious disease, and neurological disease.

* * * * *